US012672951B2

(12) United States Patent
    Eller et al.

(10) Patent No.: US 12,672,951 B2
(45) Date of Patent: Jul. 7, 2026

(54) ELECTROSPUN PTFE COATED STENT AND METHOD OF USE

(71) Applicant: Merit Medical Systems, Inc., South Jordan, UT (US)

(72) Inventors: Zeke Eller, Plano, TX (US); John William Hall, North Salt Lake, UT (US); Robert S. Kellar, Flagstaff, AZ (US); Rachel Lynn Simmons, North Salt Lake, UT (US); Robert J. Radford, Freemont, CA (US); Bart Dolmatch, Dallas, TX (US)

(73) Assignee: Merit Medical Systems, Inc., South Jordan, UT (US)

( * ) Notice: Subject to any disclaimer, the term of this patent is extended or adjusted under 35 U.S.C. 154(b) by 1065 days.

(21) Appl. No.: 17/516,069

(22) Filed: Nov. 1, 2021

(65) Prior Publication Data

US 2022/0054252 A1     Feb. 24, 2022

Related U.S. Application Data

(63) Continuation of application No. 16/877,259, filed on May 18, 2020, now Pat. No. 12,396,837, which is a
    (Continued)

(51) Int. Cl.
    *A61F 2/07*          (2013.01)
    *A61F 2/06*          (2013.01)
       (Continued)

(52) U.S. Cl.
    CPC .................. *A61F 2/06* (2013.01); *A61F 2/07* (2013.01); *A61F 2/82* (2013.01); *A61F 2/88* (2013.01); *A61L 31/10* (2013.01); *A61L*

*31/146* (2013.01); *B32B 27/322* (2013.01); *D01D 5/0007* (2013.01); *D01D 5/003* (2013.01);
(Continued)

(58) Field of Classification Search
    CPC .... A61F 2/07; A61F 2/88; A61F 2/885; A61F 2/89
    See application file for complete search history.

(56) References Cited

U.S. PATENT DOCUMENTS 2,772,444 A     12/1956   Burrows et al.
3,047,444 A      7/1962   Harwood
        (Continued)

FOREIGN PATENT DOCUMENTS

AT          366546        6/1976
CN          1823687       8/2006
        (Continued)

OTHER PUBLICATIONS

Extended European Search Report dated Mar. 30, 2016 for EP13838578.6.
        (Continued)

*Primary Examiner* — Brian A Dukert
(74) *Attorney, Agent, or Firm* — Dorsey & Whitney LLP

(57) ABSTRACT

A stent or other prosthesis may be formed by coating a single continuous wire scaffold with a polymer coating. The polymer coating may consist of layers of electrospun polytetrafluoroethylene (PTFE). Electrospun PTFE of certain porosities may permit endothelial cell growth within the prosthesis.

12 Claims, 14 Drawing Sheets

Related U.S. Application Data continuation of application No. 13/360,444, filed on Jan. 27, 2012, now Pat. No. 10,653,511.

(60) Provisional application No. 61/437,404, filed on Jan. 28, 2011.

(51) Int. Cl.

| | |
|---|---|
| *A61F 2/82* | (2013.01) |
| *A61F 2/88* | (2006.01) |
| *A61L 31/10* | (2006.01) |
| *A61L 31/14* | (2006.01) |
| *B32B 27/32* | (2006.01) |
| *D01D 5/00* | (2006.01) |
| *A61F 2/89* | (2013.01) |
| *A61F 2/915* | (2013.01) |

(52) U.S. Cl.

CPC ......... *D01D 5/0038* (2013.01); *D01D 5/0046* (2013.01); *D01D 5/0084* (2013.01); *A61F 2002/072* (2013.01); *A61F 2/89* (2013.01); *A61F 2/915* (2013.01)

(56) References Cited

U.S. PATENT DOCUMENTS

| | | | |
|---|---|---|---|
| 3,203,365 A | 8/1965 | Bowe et al. |
| 4,043,331 A | 8/1977 | Martin et al. |
| 4,044,404 A | 8/1977 | Martin et al. |
| 4,096,227 A | 6/1978 | Gore |
| 4,127,706 A | 11/1978 | Martin et al. |
| 4,223,101 A | 9/1980 | Fine et al. |
| 4,323,525 A | 4/1982 | Bornat |
| 4,345,414 A | 8/1982 | Bornat et al. |
| 4,552,707 A | 11/1985 | How |
| 4,689,186 A | 8/1987 | Bornat |
| 4,758,223 A | 7/1988 | Rydell |
| 5,167,890 A | 12/1992 | Sasshofer et al. |
| 5,172,702 A | 12/1992 | Leigh |
| 5,236,447 A | 8/1993 | Kubo |
| 5,238,430 A | 8/1993 | Wan |
| 5,328,946 A | 7/1994 | Tuminello et al. |
| 5,344,297 A | 9/1994 | Hills |
| 5,509,902 A | 4/1996 | Raulerson |
| 5,512,051 A | 4/1996 | Wang et al. |
| 5,552,100 A | 9/1996 | Shannon et al. |
| 5,562,986 A | 10/1996 | Yamamoto et al. |
| 5,601,572 A | 2/1997 | Middleman et al. |
| 5,620,763 A | 4/1997 | House et al. |
| 5,655,542 A | 8/1997 | Weilandt |
| 5,665,428 A | 9/1997 | Cha et al. |
| 5,700,572 A | 12/1997 | Klatt et al. |
| 5,702,658 A | 12/1997 | Pellegrin et al. |
| 5,741,333 A | 4/1998 | Frid |
| 5,788,651 A | 8/1998 | Weilandt |
| 5,800,389 A | 9/1998 | Burney et al. |
| 5,810,870 A | 9/1998 | Myers et al. |
| 5,842,999 A | 12/1998 | Pruitt et al. |
| 5,922,021 A | 7/1999 | Jang |
| 5,941,910 A | 8/1999 | Schindler et al. |
| D418,223 S | 12/1999 | Phipps et al. |
| 6,010,529 A | 1/2000 | Herweck et al. |
| 6,015,431 A | 1/2000 | Thornton et al. |
| 6,045,567 A | 4/2000 | Taylor et al. |
| 6,053,943 A | 4/2000 | Edwin et al. |
| 6,075,180 A | 6/2000 | Sharber et al. |
| D428,150 S | 7/2000 | Ruf et al. |
| 6,106,913 A | 8/2000 | Scardino |
| 6,126,617 A | 10/2000 | Weilandt et al. |
| 6,156,064 A | 12/2000 | Chouinard |
| 6,165,212 A | 12/2000 | Dereume et al. |
| 6,165,215 A | 12/2000 | Rottenberg et al. |
| 6,176,875 B1 | 1/2001 | Lenker et al. |
| 6,196,978 B1 | 3/2001 | Weilandt et al. |
| 6,238,430 B1 | 5/2001 | Klumb |
| 6,273,861 B1 | 8/2001 | Bates et al. |
| 6,306,424 B1 | 10/2001 | Vyakarnam |
| 6,322,523 B2 | 11/2001 | Weilandt et al. |
| D457,955 S | 5/2002 | Bilitz |
| 6,383,214 B1 | 5/2002 | Banas et al. |
| 6,419,641 B1 | 7/2002 | Mark et al. |
| 6,436,135 B1 | 8/2002 | Goldfarb |
| D463,555 S | 9/2002 | Etter et al. |
| 6,488,662 B2 | 12/2002 | Sirimanne |
| 6,497,687 B1 | 12/2002 | Blanco |
| 6,498,207 B1 | 12/2002 | Hoshikawa et al. |
| 6,517,571 B1 | 2/2003 | Brauker et al. |
| 6,656,220 B1 | 12/2003 | Gomez |
| 6,673,105 B1 | 1/2004 | Chen |
| 6,679,913 B1 | 1/2004 | Homsy |
| 6,685,736 B1 | 2/2004 | White et al. |
| 6,719,783 B2 | 4/2004 | Lentz et al. |
| D490,152 S | 5/2004 | Myall et al. |
| 6,752,826 B2 * | 6/2004 | Holloway ................. A61F 2/07 |
| | | | 623/1.13 |
| 7,041,065 B2 | 5/2006 | Weilandt et al. |
| 7,115,220 B2 | 10/2006 | Dubson et al. |
| 7,118,698 B2 | 10/2006 | Armantrout et al. |
| 7,244,272 B2 | 7/2007 | Dubson et al. |
| 7,247,160 B2 | 7/2007 | Seiler et al. |
| 7,316,754 B2 | 1/2008 | Ide et al. |
| D571,009 S | 6/2008 | Smith et al. |
| 7,413,575 B2 | 8/2008 | Phaneuf et al. |
| 7,416,559 B2 | 8/2008 | Shalaby |
| D586,916 S | 2/2009 | Faulkner et al. |
| 7,485,141 B2 | 2/2009 | Majercak et al. |
| 7,498,079 B1 | 3/2009 | Donckers |
| 7,524,527 B2 | 4/2009 | Stenzel |
| 7,556,634 B2 | 7/2009 | Lee et al. |
| D598,543 S | 8/2009 | Vogel et al. |
| 7,582,240 B2 | 9/2009 | Marin et al. |
| 7,608,048 B2 | 10/2009 | Goldenberg |
| 7,655,175 B2 | 2/2010 | Michael et al. |
| D612,044 S | 3/2010 | Scheibe |
| D612,051 S | 3/2010 | Ruf |
| D619,251 S | 7/2010 | Justiniano-Garcia et al. |
| 7,799,261 B2 | 9/2010 | Orr et al. |
| 7,857,608 B2 | 12/2010 | Fabbricante et al. |
| 7,914,568 B2 | 3/2011 | Cully et al. |
| 7,947,069 B2 | 5/2011 | Sanders |
| 7,981,353 B2 | 7/2011 | Mitchell et al. |
| 8,052,743 B2 | 11/2011 | Weber et al. |
| 8,052,744 B2 | 11/2011 | Girton |
| 8,092,768 B2 | 1/2012 | Miller et al. |
| 8,137,317 B2 | 3/2012 | Osypka |
| 8,178,030 B2 | 5/2012 | Anneaux et al. |
| 8,257,640 B2 | 9/2012 | Anneaux et al. |
| 8,262,979 B2 * | 9/2012 | Anneaux ............... A61L 31/146 |
| | | | 264/258 |
| 8,637,109 B2 | 1/2014 | Grewe et al. |
| 8,691,543 B2 | 4/2014 | Gaudette et al. |
| 8,721,711 B2 | 5/2014 | Hanson |
| 8,771,582 B2 | 7/2014 | Phaneuf et al. |
| 9,034,031 B2 | 5/2015 | Anneaux |
| 9,198,999 B2 | 12/2015 | Hall |
| 9,392,998 B2 | 7/2016 | Snow |
| 9,572,693 B2 * | 2/2017 | Cottone ................. A61F 2/915 |
| 9,655,710 B2 | 5/2017 | Eller |
| 9,775,933 B2 | 10/2017 | Knisley et al. |
| 9,856,588 B2 | 1/2018 | Anneaux |
| 10,010,395 B2 | 7/2018 | Puckett |
| 10,028,852 B2 | 7/2018 | Hall |
| 10,154,918 B2 | 12/2018 | Haselby et al. |
| 10,405,963 B2 | 9/2019 | Mcalpine |
| 10,507,268 B2 | 12/2019 | Hall et al. |
| 10,653,512 B2 | 5/2020 | Eller et al. |
| 10,675,850 B2 | 6/2020 | Hall et al. |
| 11,541,154 B2 | 1/2023 | Hall et al. |
| 2001/0009979 A1 | 7/2001 | Weilandt et al. |
| 2001/0034549 A1 | 10/2001 | Bartholf et al. |
| 2001/0039446 A1 | 11/2001 | Edwin et al. |
| 2001/0049551 A1 | 12/2001 | Tseng et al. |
| 2001/0053929 A1 | 12/2001 | Vonesh et al. |

(56) References Cited

U.S. PATENT DOCUMENTS

| | | |
|---|---|---|
| 2002/0049489 A1 | 4/2002 | Herweck et al. |
| 2002/0077693 A1 | 6/2002 | Barclay |
| 2002/0082675 A1 | 6/2002 | Myers |
| 2002/0084171 A1 | 7/2002 | Singleton et al. |
| 2002/0084178 A1 | 7/2002 | Dubson |
| 2002/0090725 A1 | 7/2002 | Simpson et al. |
| 2002/0107565 A1 | 8/2002 | Greenhalgh |
| 2002/0198588 A1 | 12/2002 | Armstrong et al. |
| 2003/0040772 A1 | 2/2003 | Hyodoh et al. |
| 2003/0050711 A1 | 3/2003 | Laurencin |
| 2003/0060871 A1 | 3/2003 | Hill et al. |
| 2003/0074049 A1 | 4/2003 | Hoganson |
| 2003/0100944 A1 | 5/2003 | Laksin et al. |
| 2003/0114917 A1 | 6/2003 | Holloway et al. |
| 2003/0139797 A1 | 7/2003 | Johnson |
| 2003/0195611 A1 | 10/2003 | Greenhalgh et al. |
| 2003/0211135 A1 | 11/2003 | Greenhalgh et al. |
| 2004/0016260 A1 | 1/2004 | Kobayashi et al. |
| 2004/0030377 A1 | 2/2004 | Dubson et al. |
| 2004/0033364 A1 | 2/2004 | Spiridigliozzi et al. |
| 2004/0038038 A1 | 2/2004 | Yeung |
| 2004/0051201 A1 | 3/2004 | Greenhalgh et al. |
| 2004/0054397 A1 | 3/2004 | Smith et al. |
| 2004/0107004 A1 | 6/2004 | Levine et al. |
| 2004/0133124 A1 | 7/2004 | Bates et al. |
| 2004/0167606 A1 | 8/2004 | Chouinard |
| 2004/0215103 A1 | 10/2004 | Mueller et al. |
| 2004/0219345 A1 | 11/2004 | Armantrout et al. |
| 2005/0053782 A1 | 3/2005 | Sen et al. |
| 2005/0054947 A1 | 3/2005 | Goldenberg |
| 2005/0125017 A1 | 6/2005 | Kudrna et al. |
| 2005/0137675 A1 | 6/2005 | Dubson et al. |
| 2005/0171593 A1 | 8/2005 | Whirley et al. |
| 2005/0187605 A1 | 8/2005 | Greenhalgh et al. |
| 2005/0244453 A1 | 11/2005 | Stucke et al. |
| 2005/0244639 A1 | 11/2005 | Marin et al. |
| 2005/0278018 A1 | 12/2005 | Jensen |
| 2006/0015138 A1 | 1/2006 | Gertner |
| 2006/0085019 A1 | 4/2006 | Cote et al. |
| 2006/0142852 A1 | 6/2006 | Sowinski et al. |
| 2006/0155210 A1 | 7/2006 | Beckman et al. |
| 2006/0200232 A1 | 9/2006 | Phaneuf et al. |
| 2006/0228435 A1 | 10/2006 | Andrady et al. |
| 2006/0233990 A1 | 10/2006 | Humphrey et al. |
| 2006/0259131 A1 | 11/2006 | Molaei et al. |
| 2006/0259137 A1 | 11/2006 | Artof et al. |
| 2006/0276874 A1 | 12/2006 | Wilson et al. |
| 2007/0023131 A1 | 2/2007 | Farnsworth et al. |
| 2007/0026036 A1 | 2/2007 | Falotico et al. |
| 2007/0027407 A1 | 2/2007 | Miller |
| 2007/0031607 A1 | 2/2007 | Dubson et al. |
| 2007/0043428 A1 | 2/2007 | Jennings et al. |
| 2007/0078472 A1 | 4/2007 | Singh |
| 2007/0087027 A1 | 4/2007 | Greenhalgh et al. |
| 2007/0123973 A1 | 5/2007 | Roth |
| 2007/0142744 A1 | 6/2007 | Provencher |
| 2007/0142771 A1 | 6/2007 | Durcan |
| 2007/0179403 A1 | 8/2007 | Heske et al. |
| 2007/0198097 A1 | 8/2007 | Zegdi |
| 2007/0207179 A1 | 9/2007 | Andersen et al. |
| 2007/0207186 A1 | 9/2007 | Scanlon et al. |
| 2007/0244569 A1 | 10/2007 | Weber et al. |
| 2007/0250037 A1 | 10/2007 | Brimhall et al. |
| 2007/0269481 A1 | 11/2007 | Li et al. |
| 2007/0276477 A1 | 11/2007 | Lee et al. |
| 2008/0021545 A1 | 1/2008 | Reneker et al. |
| 2008/0029617 A1 | 2/2008 | Marshall et al. |
| 2008/0118541 A1 | 5/2008 | Pacetti |
| 2008/0119943 A1 | 5/2008 | Armstrong et al. |
| 2008/0188923 A1 | 8/2008 | Chu |
| 2008/0199506 A1 | 8/2008 | Horres et al. |
| 2008/0200833 A1 | 8/2008 | Hardin et al. |
| 2008/0200835 A1 | 8/2008 | Monson et al. |
| 2008/0208323 A1 | 8/2008 | El-Kurdi et al. |
| 2008/0208325 A1 | 8/2008 | Helmus et al. |
| 2008/0228104 A1 | 9/2008 | Uber et al. |
| 2008/0234812 A1 | 9/2008 | Pacetti |
| 2008/0242171 A1 | 10/2008 | Huang et al. |
| 2008/0281223 A1 | 11/2008 | Goldenberg |
| 2008/0281406 A1 | 11/2008 | Addonizio et al. |
| 2008/0286321 A1 | 11/2008 | Reneker et al. |
| 2008/0288044 A1 | 11/2008 | Osborne |
| 2008/0300507 A1 | 12/2008 | Figueredo et al. |
| 2008/0305143 A1 | 12/2008 | Chen et al. |
| 2008/0319535 A1 | 12/2008 | Craven et al. |
| 2009/0012607 A1 | 1/2009 | Kim et al. |
| 2009/0018643 A1 | 1/2009 | Hashi et al. |
| 2009/0030499 A1 | 1/2009 | Bebb et al. |
| 2009/0041978 A1 | 2/2009 | Sogard et al. |
| 2009/0082846 A1 | 3/2009 | Chobotov |
| 2009/0088828 A1 | 4/2009 | Shalev et al. |
| 2009/0127748 A1 | 5/2009 | Takahashi |
| 2009/0136651 A1 | 5/2009 | Larsen et al. |
| 2009/0143698 A1 | 6/2009 | Janssens |
| 2009/0160099 A1 | 6/2009 | Huang |
| 2009/0163994 A1 | 6/2009 | Quigley et al. |
| 2009/0171456 A1 | 7/2009 | Kveen et al. |
| 2009/0227944 A1 | 9/2009 | Weber |
| 2009/0232920 A1 | 9/2009 | Lozano et al. |
| 2009/0237920 A1 | 9/2009 | Dallas et al. |
| 2009/0248131 A1 | 10/2009 | Greenan |
| 2009/0248144 A1 | 10/2009 | Bahler et al. |
| 2009/0259200 A1 | 10/2009 | Ampropoulos et al. |
| 2009/0269429 A1 | 10/2009 | Lozano et al. |
| 2009/0280325 A1 | 11/2009 | Lozano et al. |
| 2009/0299220 A1 | 12/2009 | Field et al. |
| 2009/0319034 A1 | 12/2009 | Sowinski |
| 2010/0013126 A1 | 1/2010 | Ishaque et al. |
| 2010/0036479 A1 | 2/2010 | Hill et al. |
| 2010/0042198 A1 | 2/2010 | Burton |
| 2010/0042199 A1 | 2/2010 | Burton |
| 2010/0063574 A1 | 3/2010 | Bogert |
| 2010/0076401 A1 | 3/2010 | Von Oepen et al. |
| 2010/0076543 A1 | 3/2010 | Melsheimer et al. |
| 2010/0093093 A1 | 4/2010 | Leong et al. |
| 2010/0119578 A1 | 5/2010 | To et al. |
| 2010/0129628 A1 | 5/2010 | Young |
| 2010/0130887 A1 | 5/2010 | Selis |
| 2010/0168773 A1 | 7/2010 | Funderburk et al. |
| 2010/0185156 A1 | 7/2010 | Kanner et al. |
| 2010/0190254 A1 | 7/2010 | Chian et al. |
| 2010/0193999 A1 | 8/2010 | Anneaux et al. |
| 2010/0233115 A1 | 9/2010 | Patel et al. |
| 2010/0280590 A1 | 11/2010 | Sun et al. |
| 2010/0304205 A1 | 12/2010 | Jo et al. |
| 2010/0323052 A1 | 12/2010 | Orr et al. |
| 2010/0331965 A1 | 12/2010 | Dugas et al. |
| 2011/0030885 A1 | 2/2011 | Anneaux et al. |
| 2011/0031656 A1 | 2/2011 | Anneaux et al. |
| 2011/0034656 A1 | 2/2011 | Vestberg et al. |
| 2011/0060276 A1 | 3/2011 | Schaeffer et al. |
| 2011/0087318 A1 | 4/2011 | Daugherty et al. |
| 2011/0089603 A1 | 4/2011 | Fabbricante et al. |
| 2011/0135806 A1 | 6/2011 | Grewe et al. |
| 2011/0142804 A1 | 6/2011 | Gaudette et al. |
| 2011/0152715 A1 | 6/2011 | Delap et al. |
| 2011/0156319 A1 | 6/2011 | Kurokawa et al. |
| 2011/0224715 A1 | 9/2011 | Chin et al. |
| 2011/0251631 A1 | 10/2011 | Trees et al. |
| 2011/0263456 A1 | 10/2011 | Harttig |
| 2011/0295200 A1 | 12/2011 | Speck et al. |
| 2011/0301696 A1 | 12/2011 | Mangiardi |
| 2012/0114722 A1 | 5/2012 | Ballard et al. |
| 2012/0191176 A1 | 7/2012 | Nagl et al. |
| 2012/0201988 A1 | 8/2012 | Hansen et al. |
| 2012/0220894 A1 | 8/2012 | Melsheimer |
| 2012/0225602 A1 | 9/2012 | Qi et al. |
| 2012/0271396 A1 | 10/2012 | Zheng |
| 2012/0292810 A1 | 11/2012 | Peno et al. |
| 2012/0316633 A1 | 12/2012 | Flanagan et al. |
| 2013/0018220 A1 | 1/2013 | Vad |
| 2013/0023175 A1 | 1/2013 | Anneaux et al. |
| 2013/0053948 A1 | 2/2013 | Anneaux et al. |
| 2013/0059497 A1 | 3/2013 | Anneaux et al. |

(56) References Cited

U.S. PATENT DOCUMENTS

| | | |
|---|---|---|
| 2013/0079700 A1 | 3/2013 | Ballard et al. |
| 2013/0085565 A1 | 4/2013 | Eller et al. |
| 2013/0131548 A1 | 5/2013 | Mcghie et al. |
| 2013/0150795 A1 | 6/2013 | Snow |
| 2013/0184808 A1 | 7/2013 | Hall et al. |
| 2013/0184810 A1 | 7/2013 | Hall et al. |
| 2013/0231733 A1 | 9/2013 | Knisley et al. |
| 2013/0238086 A1 | 9/2013 | Ballard et al. |
| 2013/0268062 A1 | 10/2013 | Puckett et al. |
| 2013/0316103 A1 | 11/2013 | Anneaux et al. |
| 2013/0324910 A1 | 12/2013 | Ohri et al. |
| 2013/0325109 A1 | 12/2013 | Anneaux et al. |
| 2014/0012304 A1 | 1/2014 | Lampropoulos et al. |
| 2014/0079758 A1 | 3/2014 | Hall et al. |
| 2014/0081386 A1 | 3/2014 | Haselby et al. |
| 2014/0081414 A1 | 3/2014 | Hall et al. |
| 2014/0086971 A1 | 3/2014 | Hall et al. |
| 2014/0100479 A1 | 4/2014 | Tripp et al. |
| 2014/0171826 A1 | 6/2014 | Lampropoulos et al. |
| 2014/0207021 A1 | 7/2014 | Snow |
| 2014/0265061 A1 | 9/2014 | Hall et al. |
| 2014/0273703 A1 | 9/2014 | Mower et al. |
| 2014/0283027 A1 | 9/2014 | Orona et al. |
| 2015/0045828 A1 | 2/2015 | Mcarthur et al. |
| 2015/0081000 A1 | 3/2015 | Hossainy |
| 2015/0094751 A1 | 4/2015 | Chen et al. |
| 2015/0134051 A1 | 5/2015 | Donadio et al. |
| 2015/0148459 A1 | 5/2015 | Pawloski et al. |
| 2015/0201917 A1 | 7/2015 | Snow |
| 2015/0201963 A1 | 7/2015 | Snow |
| 2015/0320542 A1 | 11/2015 | Gabriele et al. |
| 2015/0325209 A1 | 11/2015 | Ting et al. |
| 2016/0060797 A1 | 3/2016 | Anneaux et al. |
| 2016/0250048 A1 | 9/2016 | Hall et al. |
| 2016/0331528 A1 | 11/2016 | Parker |
| 2017/0273703 A1 | 9/2017 | Ding et al. |
| 2017/0360993 A1 | 12/2017 | Argentine et al. |
| 2018/0064565 A1 | 3/2018 | Mactaggart |
| 2019/0008665 A1 | 1/2019 | Hall et al. |
| 2019/0060528 A1 | 2/2019 | Skender et al. |
| 2019/0076276 A1 | 3/2019 | Longo |
| 2019/0110911 A1 | 4/2019 | Nae |
| 2020/0015987 A1 | 1/2020 | Einav |
| 2020/0369016 A1 | 11/2020 | Hall et al. |
| 2020/0369017 A1 | 11/2020 | Hall et al. |
| 2020/0375725 A1 | 12/2020 | Chobotov et al. |
| 2020/0383767 A1 | 12/2020 | Eller et al. |
| 2021/0162098 A1 | 6/2021 | Mower et al. |
| 2021/0290416 A1 | 9/2021 | Hall et al. |
| 2022/0047783 A1 | 2/2022 | Hall et al. |
| 2022/0048285 A1 | 2/2022 | Hall et al. |
| 2022/0054252 A1 | 2/2022 | Eller et al. |
| 2022/0273708 A1 | 9/2022 | Hall et al. |
| 2023/0157804 A1 | 5/2023 | Eller et al. |
| 2023/0191005 A1 | 6/2023 | Hall et al. |
| 2023/0311472 A1 | 10/2023 | Hall et al. |
| 2024/0253343 A1 | 8/2024 | Hall et al. |
| 2025/0235304 A1 | 7/2025 | Hall et al. |
| 2025/0236104 A1 | 7/2025 | Hall et al. |
| 2025/0375476 A1 | 12/2025 | Hall et al. |

FOREIGN PATENT DOCUMENTS

| | | |
|---|---|---|
| CN | 1264571 | 9/2007 |
| CN | 101584612 | 11/2009 |
| CN | 101584612 A | 11/2009 |
| CN | 102560896 A | 7/2012 |
| CN | 109157928 A | 1/2019 |
| DE | 102011012501 A1 | 8/2012 |
| EP | 0457456 | 11/1991 |
| EP | 0966920 | 4/2004 |
| EP | 1605014 | 12/2005 |
| EP | 1605014 A1 | 12/2005 |
| EP | 1679039 | 7/2006 |
| EP | 2363516 | 7/2011 |
| EP | 2363516 A1 | 9/2011 |
| EP | 2944711 B1 | 12/2017 |
| GB | 1577221 | 10/1980 |
| JP | 5140476 | 5/1975 |
| JP | 2007519491 | 7/2007 |
| JP | 2007531833 | 11/2007 |
| JP | 2009232882 | 10/2009 |
| JP | 2010517625 | 5/2010 |
| JP | 2010540190 | 12/2010 |
| JP | 2013501539 A | 1/2013 |
| JP | 2015504739 | 2/2015 |
| KR | 20100077913 | 7/2010 |
| KR | 20100108382 | 10/2010 |
| KR | 1020100108382 | 10/2010 |
| WO | 199622733 | 8/1996 |
| WO | 199800090 | 1/1998 |
| WO | 199944505 | 9/1999 |
| WO | 2002049536 | 6/2002 |
| WO | 2003051233 | 6/2003 |
| WO | 2004090206 | 10/2004 |
| WO | 2005018600 | 3/2005 |
| WO | 2005018600 A2 | 3/2005 |
| WO | 2005074547 | 8/2005 |
| WO | 2005098100 | 10/2005 |
| WO | 2006013389 | 2/2006 |
| WO | 2006123340 | 11/2006 |
| WO | 2007075256 | 7/2007 |
| WO | 2008097592 | 8/2008 |
| WO | 2009046372 | 4/2009 |
| WO | 2009127170 | 10/2009 |
| WO | 2009146280 | 12/2009 |
| WO | 2010083530 | 7/2010 |
| WO | 2010132636 | 11/2010 |
| WO | 2011017698 | 2/2011 |
| WO | 2012103501 | 8/2012 |
| WO | 2012103501 A1 | 8/2012 |
| WO | 2012122485 | 9/2012 |
| WO | 2012167216 | 12/2012 |
| WO | 2013109528 | 7/2013 |
| WO | 2013151778 | 7/2013 |
| WO | 2014007979 | 1/2014 |
| WO | 2014066297 A1 | 5/2014 |

OTHER PUBLICATIONS

Extended European Search Report dated Jun. 25, 2015 for EP12739348.6.

Extended European Search Report dated Jul. 26, 2016 for EP14741114.4.

International Report on Patentability dated Jul. 22, 2014 for PCT/US2013/021554.

International Search Report and Written Opinion dated Apr. 3, 2014 for PCT/US2013/076418.

International Search Report and Written Opinion dated Apr. 26, 2013 for PCT/US2013/021554.

International Search Report and Written Opinion dated Apr. 27, 2015 for PCT/US2015/011746.

International Search Report and Written Opinion dated Apr. 30, 2015 for PCT/US2015/012002.

International Search Report and Written Opinion dated May 1, 2014 for PCT/US2014/012043.

International Search Report and Written Opinion dated May 23, 2012 for PCT/US2012/023006.

International Search Report and Written Opinion dated Jun. 8, 2016 for PCT/US2016/019487.

International Search Report and Written Opinion dated Jun. 23, 2015 for PCT/US2013/076418.

International Search Report and Written Opinion dated Jun. 26, 2014 for PCT/US2014/024868.

International Search Report and Written Opinion dated Jul. 1, 2014 for PCT/US2014/023416.

International Search Report and Written Opinion dated Jul. 1, 2016 for PCT/US2016/020165.

International Search Report and Written Opinion dated Sep. 6, 2013 for PCT/US2013/046245.

(56) References Cited

OTHER PUBLICATIONS

International Search Report and Written Opinion dated Sep. 17, 2013 for PCT/US2013/060172.
International Search Report and Written Opinion dated Dec. 3, 2013 for PCT/US2013/060172.
International Search Report and Written Opinion dated Dec. 5, 2013 for PCT/US2013/060812.
Notice of Allowance dated Jan. 25, 2017 for U.S. Appl. No. 14/152,626.
Notice of Allowance dated Jan. 30, 2020 for U.S. Appl. No. 14/152,590.
Notice of Allowance dated Feb. 6, 2020 for U.S. Appl. No. 13/360,444.
Notice of Allowance dated Feb. 24, 2021 for U.S. Appl. No. 16/035,334.
Notice of Allowance dated Mar. 13, 2020 for U.S. Appl. No. 14/832,422.
Notice of Allowance dated Apr. 3, 2018 for U.S. Appl. No. 14/081,504.
Notice of Allowance dated Apr. 14, 2015 for U.S. Appl. No. 14/031,746.
Notice of Allowance dated May 9, 2018 for U.S. Appl. No. 15/053,232.
Notice of Allowance dated Jul. 11, 2016 for U.S. Appl. No. 13/826,618.
Notice of Allowance dated Aug. 7, 2020 for U.S. Appl. No. 14/207,344.
Notice of Allowance dated Sep. 3, 2015 for U.S. Appl. No. 13/787,327.
Notice of Allowance dated Oct. 4, 2017 for U.S. Appl. No. 14/204,466.
Notice of Allowance dated Oct. 9, 2019 for U.S. Appl. No. 13/826,618.
Notice of Allowance dated Dec. 14, 2020 for U.S. Appl. No. 14/081,715.
Notice of Allowance dated Dec. 15, 2020 for U.S. Appl. No. 15/806,020.
Office Action dated Jan. 2, 2019 for U.S. Appl. No. 13/360,444.
Office Action dated May 9, 2014 for U.S. Appl. No. 13/360,444.
Office Action dated Jun. 15, 2018 for U.S. Appl. No. 14/207,344.
Office Action dated Jun. 19, 2017 for U.S. Appl. No. 14/081,504.
Office Action dated Jun. 23, 2017 for U.S. Appl. No. 13/829,493.
Office Action dated Jun. 28, 2018 for U.S. Appl. No. 14/081,715.
Office Action dated Jun. 29, 2017 for U.S. Appl. No. 14/081,715.
Office Action dated Jun. 30, 2016 for U.S. Appl. No. 14/081,715.
Office Action dated Jul. 2, 2014 for U.S. Appl. No. 14/044,050.
Office Action dated Jul. 11, 2019 for U.S. Appl. No. 14/081,715.
Office Action dated Jul. 12, 2017 for U.S. Appl. No. 15/053,232.
Office Action dated Jul. 13, 2018 for U.S. Appl. No. 13/827,790.
Office Action dated Jul. 26, 2017 for U.S. Appl. No. 13/827,790.
Office Action dated Jul. 26, 2018 for U.S. Appl. No. 14/152,590.
Office Action dated Jul. 29, 2015 for U.S. Appl. No. 14/152,626.
Office Action dated Jul. 30, 2020 for U.S. Appl. No. 15/806,020.
European Search Report dated Dec. 13, 2024 for EP22760630.8.
European Examination Report dated Jun. 24, 2022 for EP19193202.9.
Extended European Search Report dated Jan. 7, 2022 for EP21181412.4.
Notice of Allowance dated Sep. 7, 2022 for U.S. Appl. No. 13/827,790.
Notice of Allowance dated Dec. 15, 2022 for U.S. Appl. No. 13/742,077.
Office Action dated May 12, 2022 for U.S. Appl. No. 13/827,790.
Office Action dated Aug. 5, 2021 for U.S. Appl. No. 13/827,790.
Office Action dated Nov. 9, 2022 for U.S. Appl. No. 16/877,259.
Office Action dated Dec. 24, 2021 for U.S. Appl. No. 16/877,259.
Patent Board Decision—Reversed dated Dec. 6, 2022 for U.S. Appl. No. 13/742,077.
Arras , et al., "Electrospinning of Aligned Fibers with Adjustable Orientation Using Auxiliary Electrodes", Sci. Technol. Adv. Mater., 13, Jan. 1, 2012.
Notice of Allowance dated Feb. 26, 2025 for U.S. Appl. No. 17/652,552.

Notice of Allowance dated Feb. 27, 2025 for U.S. Appl. No. 16/877,259.
Office Action dated Jan. 16, 2025 for U.S. Appl. No. 18/170,364.
Office Action dated Feb. 7, 2025 for U.S. Appl. No. 17/516,530.
Office Action dated Feb. 14, 2025 for U.S. Appl. No. 17/068,627.
Office Action dated Mar. 5, 2025 for U.S. Appl. No. 17/341,038.
European Examination Report dated Jan. 2, 2024 for EP21165437.1.
Office Action dated Jan. 24, 2024 for U.S. Appl. No. 17/652,552.
Office Action dated Nov. 29, 2023 for U.S. Appl. No. 16/895,975.
Office Action dated Dec. 13, 2023 for U.S. Appl. No. 16/896,013.
Office Action dated Dec. 19, 2023 for U.S. Appl. No. 16/877,259.
Office Action dated Dec. 29, 2023 for U.S. Appl. No. 17/068,627.
European Examination Report dated Jun. 4, 2024 for EP20199088.4.
Office Action dated Jun. 14, 2024 for U.S. Appl. No. 16/895,975.
Office Action dated Jun. 27, 2024 for U.S. Appl. No. 16/896,013.
Office Action dated Jul. 2, 2024 for U.S. Appl. No. 17/341,038.
Office Action dated Jul. 12, 2024 for U.S. Appl. No. 18/170,364.
Office Action dated Jul. 16, 2024 for U.S. Appl. No. 17/068,627.
Board Decision on Appeal dated Nov. 23, 2018 for U.S. Appl. No. 14/044,050.
EP Examination Report dated May 28, 2019 for EP12755426.9.
European Search Report dated Jan. 28, 2021 for EP20190128.7.
European Search Report dated Feb. 3, 2021 for EP20191283.9.
European Search Report dated Feb. 12, 2016 for EP13813055.4.
European Search Report dated Feb. 21, 2020 for EP19193202.9.
European Search Report dated Mar. 30, 2016 for EP13838784.0.
European Search Report dated Jun. 16, 2014 for EP14160501.4.
European Search Report dated Aug. 19, 2014 for EP12755426.9.
European Search Report dated Aug. 20, 2019 for EP14774594.7.
European Search Report dated Sep. 6, 2016 for EP14774594.7.
European Search Report dated Oct. 17, 2018 for EP16756335.2.
European Search Report dated Nov. 29, 2021 for EP21165437.1.
European Search Report dated Dec. 6, 2018 for EP13813055.4.
European Search Report dated Dec. 23, 2020 for EP20199088.4.
Office Action dated Jan. 2, 2019 for U.S. Appl. No. 14/152,590.
Office Action dated Jan. 10, 2019 for U.S. Appl. No. 13/826,618.
Office Action dated Jan. 12, 2016 for U.S. Appl. No. 14/152,590.
Office Action dated Jan. 13, 2015 for U.S. Appl. No. 13/827,790.
Office Action dated Jan. 14, 2019 for U.S. Appl. No. 13/827,790.
Office Action dated Jan. 16, 2018 for U.S. Appl. No. 14/081,715.
Office Action dated Jan. 17, 2019 for U.S. Appl. No. 14/832,422.
Office Action dated Jan. 22, 2016 for U.S. Appl. No. 14/152,626.
Office Action dated Jan. 23, 2017 for U.S. Appl. No. 14/081,715.
Office Action dated Jan. 25, 2019 for U.S. Appl. No. 14/207,344.
Office Action dated Feb. 4, 2015 for U.S. Appl. No. 13/360,444.
Office Action dated Feb. 7, 2017 for U.S. Appl. No. 13/827,790.
Office Action dated Feb. 8, 2019 for U.S. Appl. No. 14/081,715.
Office Action dated Feb. 16, 2018 for U.S. Appl. No. 13/742,077.
Office Action dated Feb. 20, 2015 for U.S. Appl. No. 14/044,050.
Office Action dated Feb. 20, 2020 for U.S. Appl. No. 15/806,020.
Office Action dated Feb. 22, 2016 for U.S. Appl. No. 13/742,077.
Office Action dated Feb. 26, 2015 for U.S. Appl. No. 14/152,590.
Office Action dated Mar. 3, 2014 for U.S. Appl. No. 13/742,025.
Office Action dated Mar. 15, 2017 for U.S. Appl. No. 14/207,344.
Office Action dated Mar. 25, 2020 for U.S. Appl. No. 14/081,715.
Office Action dated Mar. 28, 2016 for U.S. Appl. No. 13/827,790.
Office Action dated Mar. 31, 2017 for U.S. Appl. No. 14/204,466.
Office Action dated Apr. 6, 2020 for U.S. Appl. No. 13/827,790.
Office Action dated Apr. 7, 2017 for U.S. Appl. No. 13/826,618.
Office Action dated Apr. 27, 2017 for U.S. Appl. No. 13/742,077.
Office Action dated Apr. 29, 2020 for U.S. Appl. No. 14/207,344.
Office Action dated May 1, 2020 for U.S. Appl. No. 16/035,334.
Office Action dated May 11, 2018 for U.S. Appl. No. 13/826,618.
Office Action dated May 11, 2018 for U.S. Appl. No. 14/832,422.
Office Action dated May 19, 2017 for U.S. Appl. No. 13/742,025.
Office Action dated Jun. 1, 2016 for U.S. Appl. No. 14/134,280.
Office Action dated Jun. 8, 2016 for U.S. Appl. No. 14/044,050.
Office Action dated Jun. 9, 2016 for U.S. Appl. No. 14/152,626.
International Preliminary Report dated Mar. 24, 2015 for PCT/US2013/060812.

(56) References Cited

OTHER PUBLICATIONS

International Preliminary Report dated Jul. 30, 2013 for PCT/US2012/023006.
International Search Report and Written Opinion dated Jun. 26, 2014 PCT/US2014/024868.
Office Action dated May 22, 2023 for U.S. Appl. No. 16/877,259.
Office Action dated Aug. 29, 2014 for U.S. Appl. No. 14/152,590.
Office Action dated Sep. 9, 2016 for U.S. Appl. No. 14/081,504.
Office Action dated Sep. 9, 2016 for U.S. Appl. No. 14/207,344.
Office Action dated Sep. 23, 2016 for U.S. Appl. No. 14/152,590.
Office Action dated Sep. 27, 2016 for U.S. Appl. No. 13/827,790.
Office Action dated Oct. 6, 2016 for U.S. Appl. No. 13/360,444.
Office Action dated Oct. 6, 2016 for U.S. Appl. No. 13/742,025.
Office Action dated Oct. 7, 2019 for U.S. Appl. No. 13/360,444.
Office Action dated Oct. 10, 2014 for U.S. Appl. No. 13/742,025.
Office Action dated Oct. 15, 2015 for U.S. Appl. No. 13/827,790.
Office Action dated Nov. 2, 2015 for U.S. Appl. No. 13/742,077.
Office Action dated Nov. 17, 2016 for U.S. Appl. No. 13/829,493.
Office Action dated Nov. 18, 2016 for U.S. Appl. No. 13/826,618.
Office Action dated Nov. 20, 2015 for U.S. Appl. No. 13/826,618.
Office Action dated Dec. 18, 2015 for U.S. Appl. No. 14/081,504.
European Examination Report dated Mar. 15, 2024 for EP21181412.4.
Office Action dated Apr. 3, 2024 for U.S. Appl. No. 16/877,259.
Office Action dated May 7, 2024 for U.S. Appl. No. 17/652,552.
European Examination Report dated Sep. 1, 2023 for EP20190128.7.
European Examination Report dated Oct. 20, 2023 for EP21189728.5.
Office Action dated Sep. 8, 2023 for U.S. Appl. No. 17/652,552.
Office Action dated Aug. 6, 2018 for U.S. Appl. No. 13/360,444.
Office Action dated Aug. 7, 2019 for U.S. Appl. No. 15/806,020.
Office Action dated Aug. 10, 2015 for U.S. Appl. No. 14/044,050.
Office Action dated Aug. 22, 2019 for U.S. Appl. No. 14/207,344.
Office Action dated Sep. 11, 2017 for U.S. Appl. No. 14/832,422.
Office Action dated Sep. 24, 2014 for U.S. Appl. No. 14/031,746.
Office Action dated Sep. 28, 2017 for U.S. Appl. No. 14/207,344.
Office Action dated Oct. 7, 2019 for U.S. Appl. No. 14/152,590.
Office Action dated Oct. 20, 2017 for U.S. Appl. No. 13/826,618.
Office Action dated Oct. 26, 2016 for U.S. Appl. No. 13/742,077.
Office Action dated Nov. 17, 2017 for U.S. Appl. No. 13/360,444.
Office Action dated Nov. 21, 2017 for U.S. Appl. No. 14/152,590.
Office Action dated Dec. 23, 2020 for U.S. Appl. No. 13/827,790.
Office Action dated Dec. 28, 2017 for U.S. Appl. No. 13/827,790.
Office Action dated Dec. 29, 2017 for U.S. Appl. No. 14/081,504.
Shuttle® and CT-Core® Semi-Automatic Devices Updated to the website between Nov. 8, 2012-Jan. 24, 2013. Accessed website on Jun. 27, 2014 at http://www.healthcare.com/qb/int_radiplogy.html.
Arras, et al., Electrospinning of Aligned Fibers with Adjustable Orientation Using Auxiliary Electrodes, Sci. Technol. Adv. Mater., 13 ,2012.
Yasuda, et al., Contact Angle of Water on Polymer Surfaces, Am Chem, Langmuir, vol. 10 No. 7 ,1994.
European Examination Report dated May 10, 2023 for EP20191283.9.
International Search Report and Written Opinion dated Jun. 14, 2022 for PCT/US2022/070844.
Office Action dated Jun. 20, 2023 for U.S. Appl. No. 17/068,627.

Office Action dated Aug. 19, 2022 for U.S. Appl. No. 16/881,927.
Cho , et al., "Self-Healing Polymer Coatings", Advanced Materials, 21, Jan. 1, 2009 00:00:00.0, 645-649.
Takmakov , et al., "Carbon Microelectrodes with a Renewable Surface", NIH Public Access, available in PMC, Anal Chem. 82(5), Mar. 1, 2010 00:00:00.0, 2020-2028.
European Examination Report dated Mar. 24, 2025 for EP21189728.5.
European Examination Report dated Apr. 8, 2025 for EP21181412.4.
European Search Report dated Apr. 16, 2025 for EP21165437.1.
Notice of Allowance dated Apr. 10, 2025 for U.S. Appl. No. 16/877,259.
Office Action dated Apr. 10, 2025 for U.S. Appl. No. 17/515,236.
Notice of Allowance dated May 28, 2025 for U.S. Appl. No. 17/068,627.
Notice of Allowance dated Jun. 24, 2025 for U.S. Appl. No. 17/341,038.
Notice of Allowance dated Jul. 1, 2025 for U.S. Appl. No. 17/068,627.
Office Action dated Jun. 11, 2025 for U.S. Appl. No. 17/516,530.
Office Action dated Jul. 7, 2025 for U.S. Appl. No. 16/895,975.
Office Action dated Jul. 7, 2025 for U.S. Appl. No. 16/896,013.
Notice of Allowance dated Jul. 22, 2025 for U.S. Appl. No. 17/341,038.
European Search Report dated Oct. 11, 2024 for EP24173827.7.
European Search Report dated Nov. 5, 2024 for EP19193202.9.
Final Office Action dated Nov. 5, 2024 for U.S. Appl. No. 16/877,259.
Office Action dated Oct. 22, 2024 for U.S. Appl. No. 16/895,975.
Office Action dated Oct. 23, 2024 for U.S. Appl. No. 16/896,013.
Office Action dated Oct. 24, 2024 for U.S. Appl. No. 17/652,552.
European Examination Report dated Oct. 13, 2025 for EP22760630.8.
European Search Report dated Oct. 17, 2025 for EP25175405.7.
Office Action dated Oct. 21, 2025 for U.S. Appl. No. 16/895,975.
Office Action dated Oct. 21, 2025 for U.S. Appl. No. 16/896,013.
Office Action dated Oct. 28, 2025 for U.S. Appl. No. 18/068,181.
Office Action dated Dec. 4, 2025 for U.S. Appl. No. 17/516,530.
Notice of Allowance dated Jan. 22, 2026 for U.S. Appl. No. 17/515,236.
European Examination Report dated Aug. 21, 2025 for EP21165437.1.
European Search Report dated Aug. 26, 2025 for EP19193202.9.
Notice of Allowance dated Sep. 3, 2025 for U.S. Appl. No. 17/068,627.
Office Action dated Aug. 27, 2025 for U.S. Appl. No. 18/151,885.
Office Action dated Aug. 28, 2025 for U.S. Appl. No. 18/170,364.
Office Action dated Sep. 17, 2025 for U.S. Appl. No. 17/515,236.
Notice of Allowance dated Mar. 19, 2026 for U.S. Appl. No. 16/895,975.
Office Action dated Mar. 24, 2026 for U.S. Appl. No. 18/151,885.
Notice of Allowance dated Mar. 24, 2026 for U.S. Appl. No. 16/896,013.
Notice of Allowance dated Feb. 4, 2026 for U.S. Appl. No. 17/515,236.
Office Action dated Feb. 11, 2026 for U.S. Appl. No. 18/170,364.
Office Action dated Apr. 24, 2026 for U.S. Appl. No. 18/068,181.
Office Action dated Apr. 28, 2026 for U.S. Appl. No. 16/895,975.
Office Action dated May 22, 2026 for U.S. Appl. No. 17/516,530.

* cited by examiner $D_{1'}$ $D_{2'}$

ELECTROSPUN PTFE COATED STENT AND METHOD OF USE

RELATED APPLICATIONS

This application is a continuation of U.S. patent application Ser. No. 16/877,259, filed on May 18, 2020 and titled, "Electrospun PTFE Coated Stent and Methods of Use," which is a continuation of U.S. patent application Ser. No. 13/360,444, filed on Jan. 27, 2012 and tiled, "Electrospun PTFE Coated Stent and Methods of Use," now issued as U.S. Pat. No. 10,653,511, which claims priority to U.S. Provisional Application No. 61/437,404, filed on Jan. 28, 2011, and titled "Electrospun PTFE Coated Stent and Method of Use," all of which are hereby incorporated by reference in their entireties.

TECHNICAL FIELD

The present disclosure relates generally to medical devices. More specifically, the present disclosure relates to stents or other prostheses, particularly prosthesis coated by electrospun polytetrafluoroethylene (PTFE).

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figures 1, 2A, 2B, 2C:
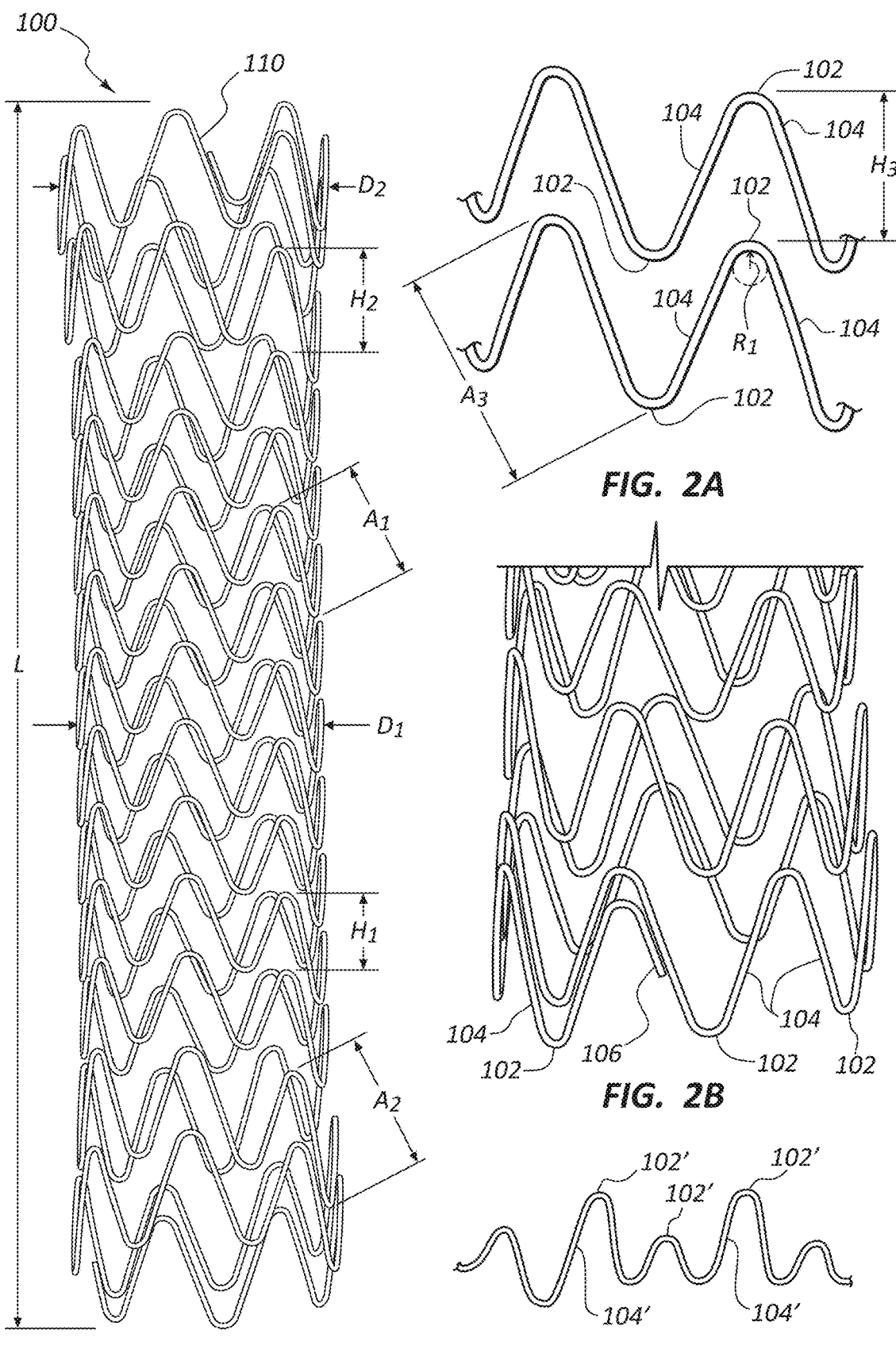
FIG. 1 is a front elevation view of one embodiment of a stent.
FIG. 2A is a cutaway view of the front portions of two adjacent coils of one embodiment of a stent.
FIG. 2B is a detail view of one end of the stent of FIG. 1.
FIG. 2C is a detail view of an alternative design of an end portion of a stent.

Stents may be deployed in various body lumens for a variety of purposes. Stents may be deployed, for example, in the central venous system for a variety of therapeutic purposes including the treatment of occlusions within the lumens of that system. It will be appreciated that the current disclosure may be applicable to stents designed for the central venous ("CV") system, peripheral vascular ("PV") stents, abdominal aortic aneurism ("AAA") stents, bronchial stents, esophageal stents, biliary stents, or any other stent. Further, the present disclosure may equally be applicable to other prosthesis such as grafts. Thus, the disclosure provided below in connection with specific examples of stents may apply analogously to other prostheses.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a stent. The proximal end of a stent is defined as the end of the stent closest to the practitioner when the stent is disposed within a deployment device which is being used by the practitioner. The distal end is the end opposite the proximal end, along the longitudinal direction of the stent, or the end furthest from the practitioner. It is understood that, as used in the art, these terms may have different meanings once the stent is deployed (i.e. the "proximal" end may refer to the end closest to the head or heart of the patient depending on application). For consistency, as used herein, the ends of the stent labeled "proximal" and "distal" prior to deployment remain the same regardless of whether the stent is deployed. The longitudinal direction of the stent is the direction along the axis of a generally tubular stent. In embodiments where a stent is composed of a metal wire structure coupled to a polymer layer, the metal structure is referred to as the "scaffolding" and the polymer layer as the "coating." The term "coating" may refer to a single layer of polymer, multiple layers of the same polymer, or layers comprising distinct polymers used in combination.

Lumens within the central venous system are generally lined with endothelial cells. This lining of endothelial cells throughout the central venous system makes up the endothelium. The endothelium acts as an interface between blood flowing through the lumens of the central venous system and the inner walls of the lumens. The endothelium, among other functions, reduces or prevents turbulent blood flow within the lumen.

A therapeutic stent which includes a coating of porous or semi-porous material may permit the formation of an endothelial layer on the inside surface of the stent. A stent which permits the formation of the endothelium within the stent may further promote healing at the therapeutic region. For example, a stent coated with endothelial cells may be more consistent with the surrounding body lumens, thereby resulting in less turbulent blood flow or a decreased risk of thrombosis, or the formation of blood clots. A stent which permits the formation of an endothelial layer on the inside surface of the stent may therefore be particularly biocompatible, resulting in less trauma at the point of application and fewer side effects.

Electrospun polytetrafluoroethylene (PTFE) may be used as a stent coating where endothelial cell growth is desirable. "Electrospinning" refers to a process for forming mats, tubes, or other shapes by depositing small strings of PTFE on charged surfaces. The electrospinning process controls the thickness, density, porosity, and other characteristics of the PTFE so formed. Electrospinning of PTFE is described in United States Patent Application, Publication No. US 2010/0193999, which is incorporated herein by reference.

The present disclosure relates to a stent which has, in certain embodiments, metal scaffolding coated with at least one layer of electrospun PTFE. It will be appreciated that, though particular structures and coatings are described below, any feature of the scaffolding or coating described below may be combined with any other disclosed feature without departing from the scope of the current disclosure. For example, certain figures show metal scaffolding without any coating; the features described and illustrated in those figures may be combined with any combination of coatings disclosed herein.

Figure 3:
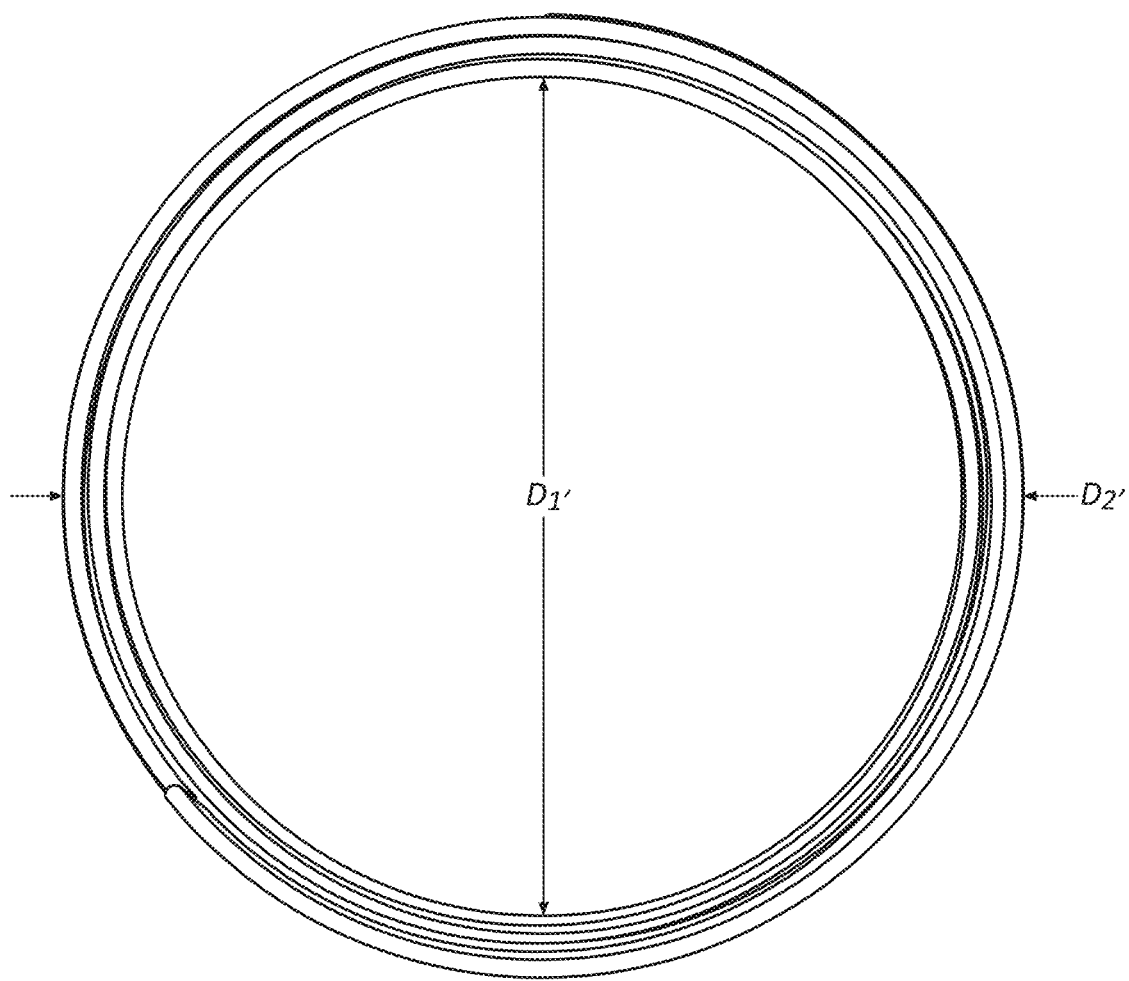
FIG. 3 is a top view of another embodiment of a stent with flared ends.
Figure 4:
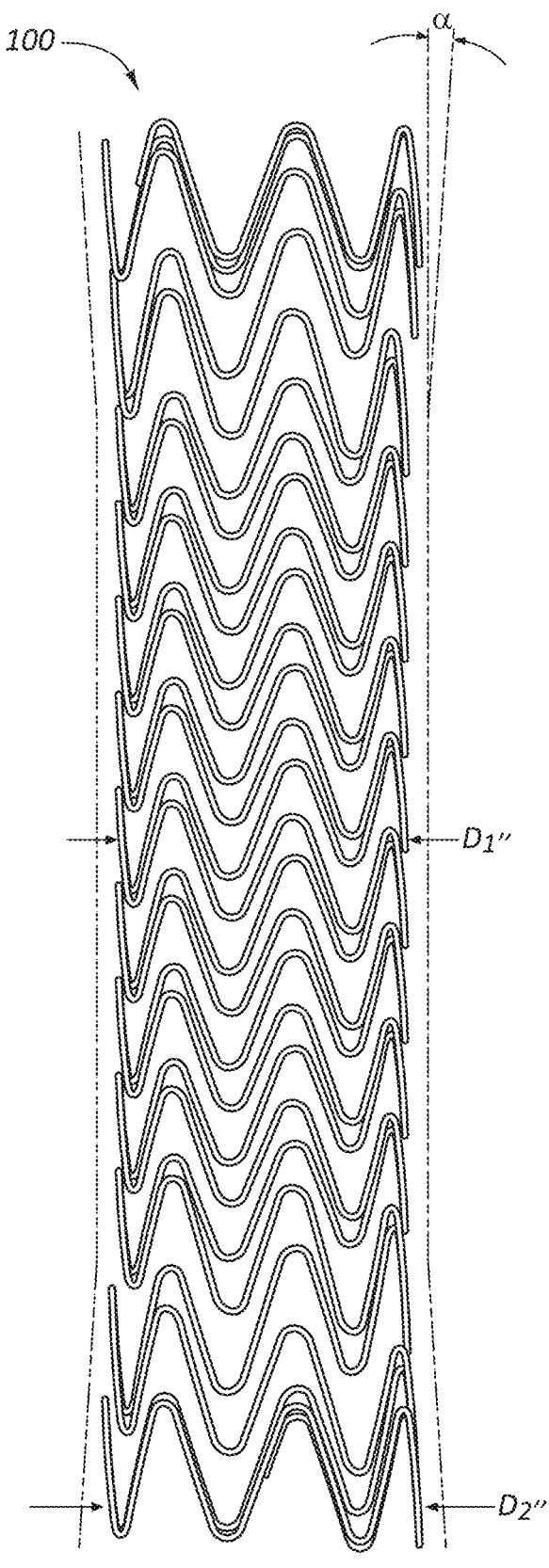
FIG. 4 is a front elevation view of the stent of FIG. 3.
Figure 5:
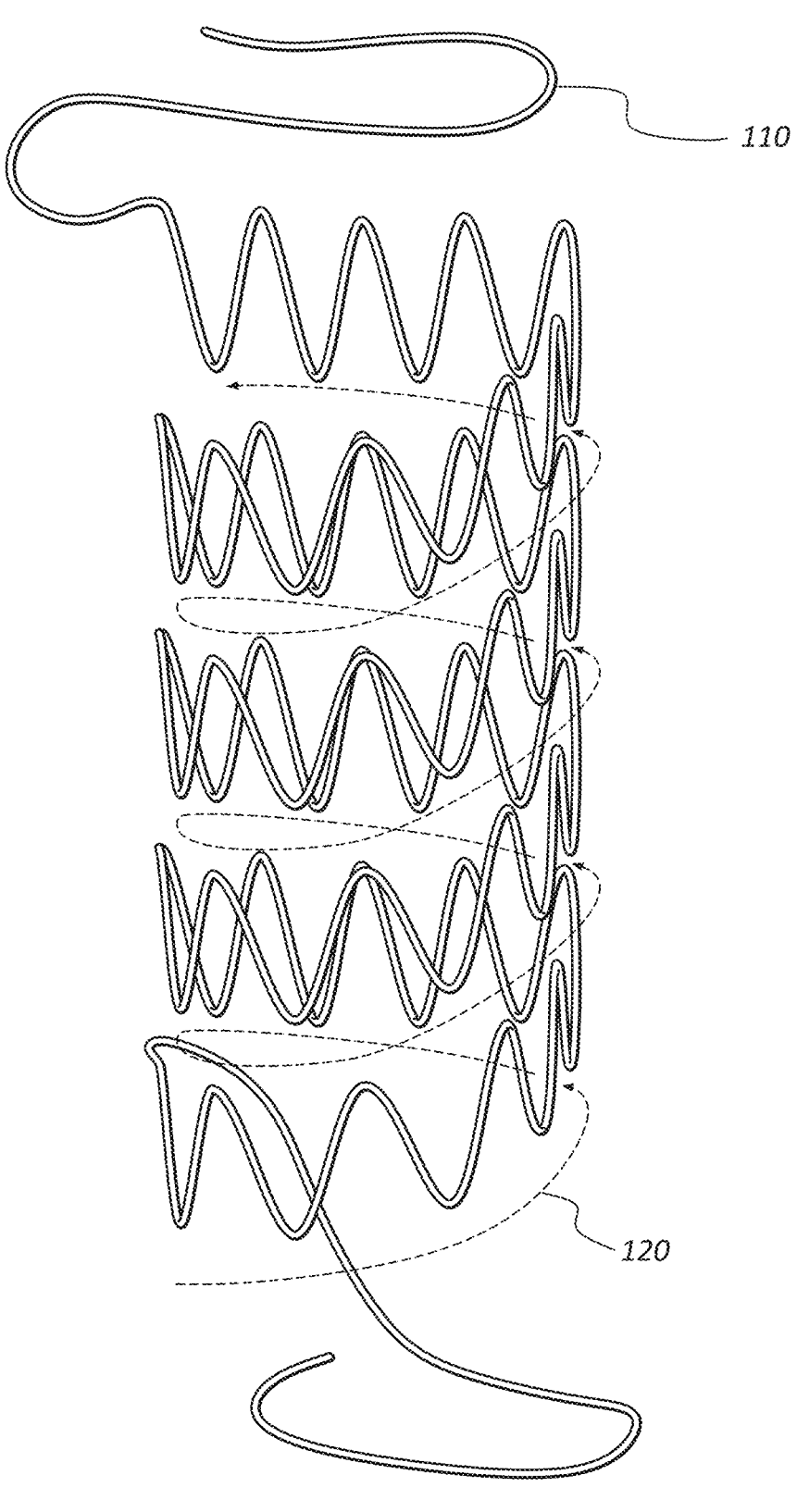
FIG. 5 is a perspective view of one embodiment of a stent, illustrating how a wire may be shaped to form the structure of the stent.
Figure 6A:
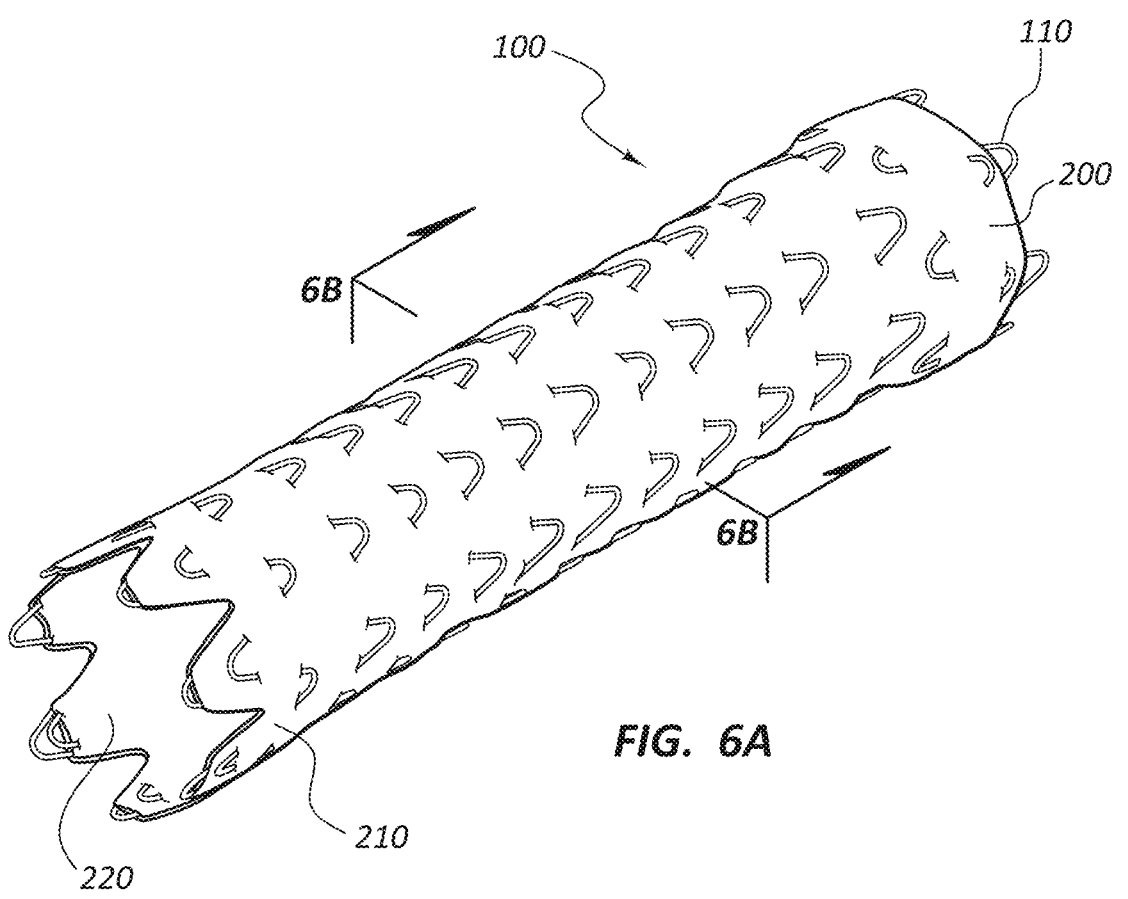
FIG. 6A is a perspective view of a covered stent.
Figure 6B:
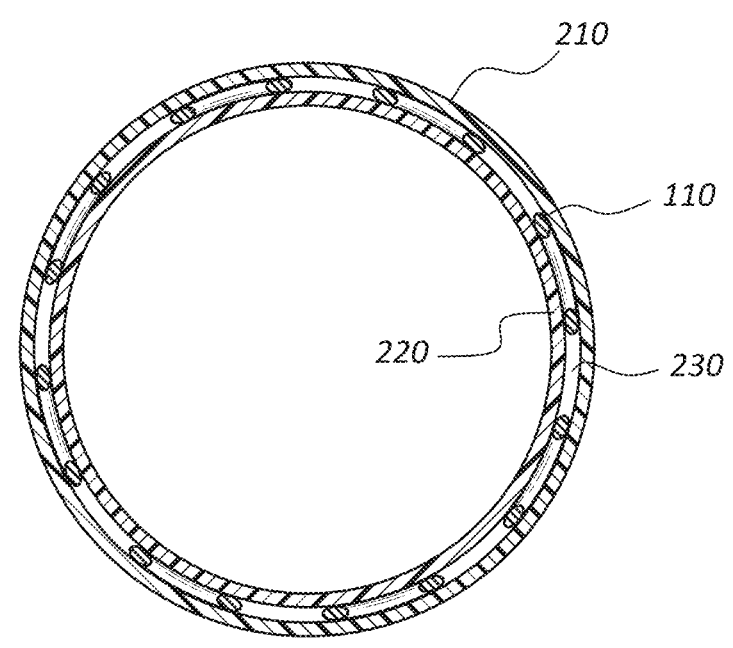
FIG. 6B is a cross sectional view of the stent of FIG. 6A along the plane 6B-6B.
Figure 7:
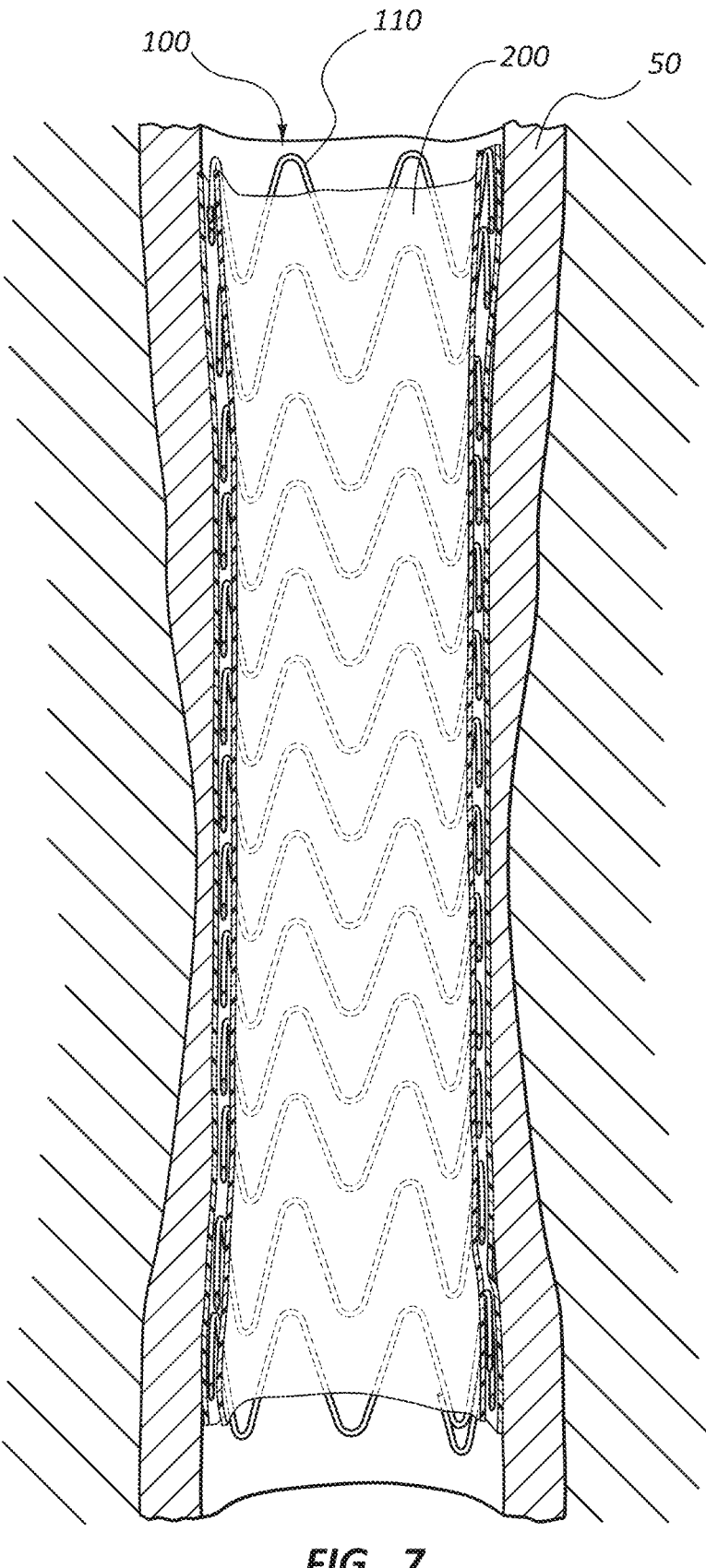
FIG. 7 illustrates one embodiment of a stent deployed in a body lumen.

FIGS. 1, 2A, and 2B show views of a possible embodiment of a stent. FIGS. 3 and 4 are views of one embodiment of a stent which includes flared ends. FIG. 5 illustrates one embodiment of how a wire may be shaped to form a scaffold for a stent. FIGS. 6A and 6B illustrate an embodiment of a covered stent. FIG. 7 illustrates a stent deployed within a body lumen. Finally, FIGS. 8A-11D are scanning electron micrographs (SEMs) of possible coatings for stents. As indicated above, it will be understood that, regardless of whether the stent illustrated in any particular figure is illustrated with a particular coating, or any coating at all, any embodiment may be configured with any of the combinations of coatings shown or described herein.

FIG. 1 illustrates a front elevation view of an embodiment of a stent 100. The illustrated embodiment depicts one embodiment of a configuration for a metal wire 110 forming a scaffolding structure. As depicted in FIG. 1, the scaffolding may consist of a single continuous wire.

Referring generally to FIGS. 1, 2A, and 2B, particular features of the illustrated stent are indicated. It will be appreciated that the numerals and designations used in any figure apply to analogous features in other illustrated embodiments, whether or not the feature is so identified in each figure. As generally shown in these Figures, the stent 100 may consist of a wire 110 shaped to form scaffolding. The wire 110 may be shaped in a wave-type configuration, the waves defining apexes 102 and arms 104 of the stent. The scaffolding may further be coupled to a covering layer (not pictured). Additionally, in some embodiments, any covering as disclosed herein may be applied to any type of scaffolding or stent frame, for example, laser cut stent frames, polymeric stent frames, wire scaffolding, and so forth.

The stent 100 may be designed such that the midsection of the stent is "harder" than the ends. The "hardness" of the stent refers to the relative strength of the stent (e.g., its compressibility). A harder portion of the stent will have greater strength (i.e. exert a greater radial outward force) than a softer portion. In one embodiment, the midsection of the stent is harder than the proximal and distal end sections which are relatively softer.

Four basic design parameters may be manipulated to influence the properties (hardness, strength, crush force, hoop force, flexibility, etc.) of the illustrated stent. These properties are: (1) apex to apex distance, designated as $H_x$ in FIGS. 1 and 2A; (2) arm length, designated as $A_x$ in FIGS. 1 and 2A; (3) apex radius, designated as $R_x$ in FIG. 2A; and (4) the diameter of the scaffolding wire 110. These values may or may not be constant at different points on a stent. Thus, the subscript "x" is used generically; that is, each distance identified as "H" refers to an apex to apex distance with subscripts 1, 2, 3, etc., signifying the apex to apex distance at a particular point. It will be appreciated that these subscript designations do not necessarily refer to a specific distance, but may be used relatively (i.e., $H_1$ may be designated as smaller than $H_2$ without assigning any precise value to either measurement). Further, as will be apparent to one skilled in the art having the benefit of this disclosure, an analogous pattern of measurements and subscripts is employed for other parameters described herein, for example $A_x$ and $R_x$.

The overall stent design may be configured to optimize desired radial force, crush profile, and strain profile. The stent design parameters may each be configured and tuned to create desired stent characteristics. For example, the strain profile may be configured to be less than the failure point for the material being used.

A first parameter, the apex to apex distance, is designated as $H_x$. This measurement signifies the distance between a first apex and a second apex where both apexes substantially lie along a line on the outside diameter of the stent which is co-planar with, and parallel to, the longitudinal axis of the stent. In some embodiments, $H_x$ may be constant along the entire length of the stent. In other embodiments the length of the stent may be divided into one or more "zones" where $H_x$ is constant within a zone, but each zone may have a different $H_x$. In still other embodiments $H_x$ may vary along the entire length of the stent. $H_x$ may be configured, in connection with the other design parameters, to determine the properties of the stent. Generally, regions of the stent with a smaller $H_x$ value will be harder than regions with a larger $H_x$ value.

In the embodiment illustrated in FIG. 1, there are two "flare zones" at either end of the stent and a midbody zone along the remaining length of the stent. In the illustrated embodiment, $H_1$ designates the apex to apex distance in the midbody zone of the stent and $H_2$ designates the apex to apex distance in the flare zones of the stent. In the illustrated embodiment, the apex to apex distance, $H_2$, is the same in both the flare zone near the distal end of the stent and the flare zone near the proximal end of the stent. In some embodiments $H_1$ may be smaller than $H_2$, resulting in a stent that is relatively harder in the midbody and relatively softer on the ends. A stent with such properties may be utilized in applications where strength is necessary along the midbody, for example to treat a tumor or other occlusion, but the ends are configured to rest on healthy tissue where softer ends will minimize trauma to the healthy tissue.

In embodiments where soft ends and a hard midbody are desirable, $H_1$ may be between about 2 mm and 30 mm and $H_2$ between about 2.1 mm and 30.1 mm. For example, in stents for CV or PV application, $H_1$ may be between about 3 mm and 10 mm and $H_2$ between about 3.1 mm and 10.1 mm, such as: 3 mm<$H_1$<8 mm and 3.5 mm<$H_2$<9 mm; 3 mm<$H_1$<6.5 mm and 4 mm<$H_2$<8 mm; or 3 mm<$H_1$<5 mm and 5.5 mm<$H_2$<6.5 mm.

In other embodiments where two or more apex to apex lengths are present in one stent, the change in apex to apex length may be correlated to the displacement of the apexes from the midpoint of the stent. In other words, the apex to apex length may increase incrementally as one moves away from the midpoint of the stent toward the ends in a manner that gives the stent the same geometry, and therefore the same properties, on either side of the midpoint of the length of the stent. In other embodiments, different geometries may be utilized at any point along the length of the stent. It will be appreciated that the ranges of values for $H_x$ disclosed above apply analogously to embodiments where the stent has multiple apex to apex lengths. For example, in one embodiment a stent may have an apex to apex length at midbody within one of the ranges disclosed above for $H_1$, and the value of $H_x$ may vary incrementally, in steps, or some other pattern, along the length of the stent reaching an apex to apex length at the ends within the complimentary range for $H_2$.

Moreover, in some embodiments, the value of $H_x$ may be small enough that adjacent coils are "nested" within each other. In other words, the apexes of a first helical coil may extend up into the spaces just below the apexes of the next adjacent coil. In other words, apexes of lower coils may extend a sufficient amount so as to be disposed between the arms of higher coils. In other embodiments the value of $H_x$ may be large enough that adjacent coils are completely separated. In embodiments wherein adjacent coils are "nested," the number of wires at any particular cross section of the stent may be higher than a non-nested stent. In other words, cutting the stent along an imaginary plane disposed orthogonal to the longitudinal axis of the stent will intersect more wires if the stent is nested as compared to non-nested stents. The smaller the value of $H_x$, the more rows may be intersected by such a plane (that is, more than just the next adjacent row may extend into the spaces below the apexes of a particular row). Nested stents may create relatively higher strains in the scaffolding structure when the stent is loaded into a delivery catheter. In some instances the delivery catheter for a nested stent may therefore be relatively larger than a delivery catheter configured for a non-nested stent. Further, nested stents may be relatively stiff as compared to non-nested stents with similar parameters.

As will be apparent to those skilled in the art having the benefit of this disclosure, stents with a hard mid body and soft ends may be desirable for a variety of applications. Further, in some instances a basically "symmetric" stent may be desirable; in other words, a stent with certain properties at the midbody section and other properties at the ends, where the properties at both ends are substantially identical. Of course, other embodiments may have varied properties along the entire length of the stent. It will be appreciated that while the effect of changing variables, for instance the difference between $H_1$ and $H_2$, may be described in connection with a substantially symmetric stent (as in FIG. 1) the same principles may be utilized to control the properties of a stent where the geometry varies along the entire length of the stent. As will be appreciated by those skilled in the art having the benefit of this disclosure, this applies to each of the variable parameters described herein, for example $H_x$, $A_x$, and $R_x$.

A second parameter, arm length, is designated as $A_x$ in FIGS. 1 and 2A. As with $H_x$, $A_x$ may be constant along the length of the stent, be constant within zones, or vary along the length of the stent. Variations in the length of $A_x$ may be configured in conjunction with variations in the other parameters to create a stent with a particular set of properties. Generally, regions of the stent where $A_x$ is relatively shorter will be harder than regions where $A_x$ is longer.

In some embodiments, the arm length $A_1$ near the midsection of the stent 100 will be shorter than the arm length $A_2$ near the ends. This configuration may result in the stent being relatively harder in the midsection. In embodiments where soft ends and a hard midbody are desirable, $A_1$ may be between about 2 mm and 30 mm and $A_2$ between about 2.1 mm and 30.1 mm. For example, in stents for CV or PV application, $A_1$ may be between about 2 mm and 10 mm and $A_2$ between about 2.1 mm and 10.1 mm, such as: 2.5 mm<<8 mm and 3 mm<$A_2$<9 mm; 3 mm<<6 mm and 4 mm<$A_2$<7.5 mm; or 4 mm<$A_1$<5 mm and 5 mm<$A_2$<6 mm.

In other embodiments where two or more arm lengths are present in one stent, the change in arm length may be correlated to the displacement of the arm from the midpoint along of the stent. In other words, the arm length may increase incrementally as one moves away from the midpoint of the stent toward the ends in a manner that gives the stent the same geometry, and therefore the same properties, on either side of the midpoint of the length of the stent. In other embodiments, different geometries may be utilized at any point along the length of the stent. It will be appreciated that the ranges of values for $A_x$ disclosed above apply analogously to embodiments where the stent has multiple arm lengths. For example, in one embodiment a stent may have an arm length at midbody within one of the ranges disclosed above for $A_1$, and the value of $A_x$ may vary incrementally, in steps, or some other pattern, along the length of the stent reaching an arm length at the ends within the complimentary range for $A_2$.

A third parameter, the apex radius, is designated as $R_1$ in FIG. 2A. As with $H_x$, and $A_x$, $R_x$ may be configured in order to create desired properties in a stent. In some embodiments, the inside radius of each apex may form an arc with has a substantially constant radius. As shown by a dashed line in FIG. 2A, this arc can be extended to form a circle within the apex. The measurement $R_x$ refers to the radius of the arc and circle so described. Further, in some embodiments the arms and apexes of the stent scaffolding are formed by molding a wire around pins protruding from a mandrel. The radius of the pin used gives the apex its shape and therefore has substantially the same radius as the apex. In some embodiments $R_x$ will be constant along the entire length of the stent, be constant within zones along the length of the stent, or vary along the entire length of the stent. Variations in the magnitude of $R_x$ may be configured in conjunction with variations in the other parameters to create a stent with a particular set of properties. Generally, regions of the stent where $R_x$ is relatively smaller will be harder than regions where $R_x$ is larger.

Furthermore, in some instances, smaller values of $R_x$ may result in relatively lower strain in the wire scaffolding when the scaffolding is compressed, for example when the stent is disposed within a delivery catheter. Moreover, wires of relatively larger diameters may result in relatively lower strain at or adjacent the radius measured by $R_x$ when compressed, as compared to wires of smaller diameters. Thus, in some instances, the strain may be optimized for a particular design by varying the value of $R_x$ and the diameter of the wire forming the scaffolding.

Like the other variables, $R_x$ may take on a range of values depending on the application and the desired properties of the stent. In some embodiments $R_x$ may be between about 0.25 mm and 1.5 mm. For example, in stents for CV or PV application, $R_x$ may be between about 0.35 mm and 0.70 mm, such as: 0.35 mm<$R_x$<0.65 mm; 0.35 mm<$R_x$<0.6 mm; or 0.4 mm<$R_x$<0.5 mm.

It will be appreciated that the disclosed ranges for $R_x$ apply whether the value of $R_x$ is constant along the length of the stent, whether the stent is divided into zones with different $R_x$ values, or whether $R_x$ varies along the entire length of the stent.

The fourth parameter, wire diameter, is discussed in detail in connection with FIG. 5 below.

FIG. 2A illustrates a cutaway view of the front portions of two adjacent coils of a stent. The portions of the coils depicted are meant to be illustrative, providing a clear view of the three parameters $H_x$, $A_x$, and $R_x$. It will be appreciated that all three of these parameters may be configured in order to create a stent with particular properties. Any combination of the values, ranges, or relative magnitudes of these parameters disclosed herein may be used within the scope of this disclosure. As an example of these values taken together, in one embodiment of a CV or PV stent with a relatively hard midbody and softer ends, $H_1$ may be about 4 mm and $H_2$ about 5.9 mm; $A_1$ may be about 4.5 mm and $A_2$ about 5.6 mm; and $R_1$ about 0.5 mm.

FIG. 2B is a close up view of one end of a stent. In embodiments where the scaffolding is formed by a single continuous wire, FIG. 2B illustrates one way in which the end of the wire 106 may be coupled to the scaffolding. As illustrated, the wire may be disposed such that the final coil approaches and runs substantially parallel to the previous coil. This configuration results in the apex to apex distance between the two coils decreasing near the end 106 of the wire. In some embodiments this transition will occur along the distance of about 4-8 apexes along the length of the wire. For example, if a stent is configured with a apex to apex spacing of $H_2$' along the region of the stent nearest the ends, the apex to apex distance will decrease from $H_2$' to a smaller distance which allows the end of the wire 106 to meet the prior coil (as illustrated in FIG. 2B) over the course of about 4-8 apexes.

FIG. 2C illustrates an alternative configuration of a wire scaffolding. In the embodiment of FIG. 2C, apexes 102' alternate in relative height along the length of the wire. In particular, in the embodiment shown, the apexes form a pattern comprising a higher apex, a shorter apex, a higher apex, a shorter apex, and so on, around the helical coil. In some instances, a stent may be configured with alternating apexes at one or both ends of the stent. For example, a stent as shown in FIG. 1 may be configured with the pattern of apexes 102' and arms 104' shown in FIG. 2C at one or both ends of the stent. Such an alternating pattern of apexes may distribute the force along the vessel wall at the ends of the stent, thus creating relatively a-traumatic ends.

The end 106 may be attached to the scaffolding in a variety of ways known in the art. The end 106 may be laser welded to the scaffolding or mechanically crimped to the scaffolding. In embodiments where the stent includes a polymer cover, the end 106 may be secured by simply being bound to the cover. In other instances, a string may be used to bind or tie the end 106 to adjacent portions of the scaffolding. Similarly, in some instances, a radiopaque marker may be crimped around the end 106 in such a manner as to couple the end 106 to the scaffolding. Additionally other methods known in the art may be utilized.

Furthermore, in some embodiments the stent 100 may be configured with radiopaque markers at one or more points along the stent 100. Such markers may be crimped to the scaffolding structure. In other embodiments a radiopaque ribbon, for example a gold ribbon, may be threaded or applied to the stent 100. In some embodiments these markers may be located at or adjacent one or both ends of the stent 100. Any radiopaque material may be used, for example gold or tantalum.

Referring again to FIG. 1 as well as to FIGS. 3 and 4, the stent 100 may be configured with flared ends. It will be appreciated that in certain embodiments a stent may have a flare at both the proximal and distal ends, only at the proximal end or only at the distal end, or at neither end. In certain of these embodiments the stent 100 may have a substantially constant diameter in the midbody zone of the stent, with the ends flaring outward to a larger diameter at the ends. It will be appreciated that the geometry of the flares at the proximal and distal ends may or may not be the same.

In the embodiment illustrated in FIG. 1, the stent 100 has a diameter, $D_1$, at the midbody of the stent. This diameter may be constant along the entire midbody of the stent. The illustrated embodiment has a second diameter, $D_2$, at the ends. This change in diameter creates a "flare zone" at the end of the stent, or an area in which the diameter is increasing and the stent therefore may be described as including a "flared" portion. In some embodiments the flare zone will be from about 1 mm to 60 mm in length. For example in certain stents designed for CV or PV application the flare zone may be from about 3 mm to about 25 mm in length, such as: from about 4 mm to 15 mm, or from about 5 mm to about 10 mm in length.

FIGS. 3 and 4 also illustrate how a stent may be flared at the ends. Diameters $D_1$' and $D_1$" refer to midbody diameters, analogous to $D_1$, while $D_2$' and $D_2$" refer to end diameters analogous to $D_2$. Further, as illustrated in FIG. 4, the flared end may create an angle, alpha, between the surface of the stent at the midbody and the surface of the flare. In some instances the flare section will uniformly flare out at a constant angle, as illustrated in FIG. 4. In some embodiments angle alpha will be from about 1 degree to about 30 degrees. For example, in some stents designed for CV or PV application, alpha will be from about 2 degrees to 8 degrees, such as: from about 2.5 degrees to about 7 degrees or from about 3 degrees to about 5 degrees. In one exemplary embodiment alpha may be about 3.6 degrees.

The stent 100 of FIG. 1 also has a length L. It will be appreciated that this length can vary depending on the desired application of the stent. In embodiments where the stent has flare zones at the ends, longer stents may or may not have proportionally longer flare zones. In some embodiments, this flare zone may be any length described above, regardless of the overall length of the stent.

It will be appreciated that the disclosed stent may be formed in a variety of sizes. In some embodiments, L may be from about 20 mm to about 200 mm. For example, in CV applications the stent may have a length, L, of from about 40 mm to 100 mm or any value between, for example, at least about 50 mm, 60 mm, 70 mm, 80 mm, or 90 mm. In PV applications the stent may have a length, L, of from about 25 mm to 150 mm or any value between, for example at least about 50 mm, 75 mm, 100 mm or 125 mm. The stent may also be longer or shorter than these exemplary values in other stent applications.

Likewise the stent may be formed with a variety of diameters. In some embodiments the midbody diameter of the stent may be from about 4 mm to about 40 mm. For example, in CV or PV applications the stent may have a midbody inside diameter of about 3 mm to 16 mm or any distance within this range such as between about 5 mm to 14 mm or between about 7 mm to about 10 mm.

The stent may or may not be configured with flared ends regardless of the midbody diameter employed. In some central venous embodiments the maximum diameter at the flared end will be between about 0.5 mm to about 2.5 mm greater than the midbody diameter. For example, the maximum diameter at the flared end may be between about 1 mm to about 2 mm, or alternatively between about 1.25 mm and about 1.5 mm, such as about 1.25 mm or about 1.5 mm greater than the midbody diameter.

Referring now to FIG. 5, the scaffolding of the stent may be formed from a single continuous wire. In some embodiments the wire may be comprised of Nitinol (ASTM F2063), or other suitable materials. In some embodiments the wire will have a diameter between about 0.005 inches and about 0.020 inches. For example, in some stents designed for CV or PV application, the wire diameter may be from about 0.008 inches to about 0.012 inches in diameter including certain embodiments where the wire is from about 0.009 inches to about 0.011 inches in diameter or embodiments where the wire is about 0.010 inches in diameter. Furthermore stents configured for the thoracic aorta may be formed of wires up to 0.020 inches in diameter, including wires up to about 0.015 inches or 0.010 inches in diameter.

FIG. 5 illustrates how, in some embodiments, the wire 110 may be wound in a helical pattern creating coils that incline along the length of the stent. The waves of the wire which form the arms and apexes may be centered around this helix, represented by the dashed line 120.

Referring now to FIGS. 6A and 6B, in some embodiments the stent 100 may be comprised of a wire 110 which forms the scaffolding and a cover 200 coupled to the scaffolding. In some embodiments this cover may be comprised of a single layer, while in other embodiments it may be comprised of 2, 3, or more layers of material. One or more layers may be comprised of a polymer.

The illustrated embodiment has two cover layers, an outer layer 210 and an inner layer 220. Portions of the scaffolding may protrude through one or both layers at certain points, or, the scaffolding may be completely enclosed on the outside diameter by the outer layer 210 and on the inside diameter by the inner layer 220.

In some embodiments the outer layer 210, the inner layer 220, or both may be comprised of electrospun PTFE. Electrospun PTFE consists of tubes, mats, or other shapes of PTFE formed from randomly deposited strings of PTFE. As previously indicated, electrospinning of PTFE is described in United States Patent Application, Publication No. US 2010/0193999. As described in the reference, electrospinning may comprise depositing a polymer on a collection surface, in the presence of an electrostatic field. In some instances the polymer may be electrostatically charged and may be discharged through one or more orifices.

Further information, which is unique to this disclosure, relative to electrospinning PTFE or other polymer is included below. The properties of electrospun PTFE, including density and porosity, may be controlled or influenced during the creation of the electrospun PTFE, through controlling the electrospinning process.

In some embodiments, a PTFE dispersion may be discharged through an orifice to electrospin the PTFE. Furthermore, in some exemplary embodiments polyethylene oxide (PEO) may be added to the PTFE dispersion prior to electrospinning the material. The PEO may be added as a fiberizing agent, to aid in the formation of PTFE fibers within the dispersion or during the process of electrospinning the material. In some instances the PEO may more readily dissolve in the PTFE dispersion if the PEO is first mixed with water. In some examples this increased solubility may reduce the time needed to dissolve PEO in a PTFE dispersion from as long as multiple days to as little as 30 minutes. After the material is electrospun onto a collector, the material may then be sintered as further described below. In some instances the sintering process will tend to set or harden the structure of the PTFE. Furthermore, sintering may also eliminate the water and PEO, resulting in a mat of substantially pure PTFE.

In one exemplary process, a 60 wt % PTFE water dispersion was mixed with PEO and water as follows. First 5 mL of water was added to 1.4 g of PEO. The water and PEO were mixed until the PEO was fully dissolved and the solution created a thick gel. 30 mL of 60 wt % PTFE was then added to the PEO/water mixture. The combined solution was then allowed to sit or mix in a non-agitating jar roller until the solution achieved homogeneity. In other examples, the water, PEO, and PTFE amounts may be controlled to optimize the viscosity, PEO/PTFE ratio, or other properties of the mixture. In some instances adding water to the PEO before mixing with the PTFE dispersion may aid in reducing the number of large solid chunks in the mixture, lower the preparation time for the mixtures, and reduce the time needed for the combined mixture to solubilize.

Membranes composed of electrospun PTFE may have a microstructure composed of many fibers crossing and each other at various and random points. The electrospinning process may control the thickness of this structure and, thereby the relative permeability of the membrane. As more and more strands of PTFE are electrospun onto a membrane, the membrane may both increase in thickness and decrease in permeability (due to successive layers of strands occluding the pores and openings of layers below). (This microstructure is shown in FIGS. 9A-11D which are discussed in more detail below.)

The complex and random microstructure of electrospun PTFE presents a challenge to the direct measurement of the average pore size of the membrane. Average pore size can be indirectly determined by measuring the permeability of the membrane to fluids using known testing techniques and instruments. Once the permeability is determined, that measurement may be used to determine an "effective" pore size of the electrospun PTFE membrane. As used herein, the "pore size" of an electrospun PTFE membrane refers to the pore size of a membrane which corresponds to the permeability of the electrospun PTFE when measured using ASTM standard F316 for the permeability measurement. This standard is described in ASTM publication F316 "Standard Test Methods for Pore Size Characteristics of Membrane Filters by Bubble Point and Mean Flow Pore Test," which is incorporated herein by reference.

In some applications it may be desirable to create a stent 100 with an outer layer 210 which is substantially impermeable. Such a layer may decrease the incidence of lumen tissue surrounding the stent growing into the stent. This may be desirable in applications where the stent is used to treat stenosis or other occlusions; an impermeable outer layer may prevent tissue from growing into the lumen of the stent and reblocking or restricting the body lumen. In some embodiments a substantially impermeable outer layer may be produced by using electrospun PTFE with an average pore size of about 0 microns to about 1.5 microns. In other embodiments, the impermeable layer may have an average pore size less than about 0.5 microns. In yet other embodiments, the impermeable layer may have an average pore size less than about 1.0 microns. In some embodiments, the impermeable layer may be a layer other than the outer layer, such as a tie layer, an intermediate layer or an inner layer. Furthermore, a substantially impermeable layer may be formed of fluorinated ethylene proplyene (FEP) which is applied, for example, as a film or dip coating. Furthermore, FEP may be electrospun with a small average pore size to create a substantially impermeable layer.

In other potential embodiments it may be desirable to create a stent with an outer layer 210 which is more porous. A porous outer layer 210 may permit healing and the integration of the prosthesis into the body. For instance, tissue of the surrounding lumen may grow into the porous outer diameter. This "tissue ingrowth" may permit healing at the therapy site. In some embodiments a porous outer layer 210 may be formed of electrospun PTFE.

In certain embodiments a relatively porous inner layer 220 may be desirable. This layer may or may not be used in conjunction with a substantially impermeable outer layer 210. A relatively porous inner layer may permit endothelial grown on the inside diameter of the stent 100 which may be desirable for healing, biocompatibility, and reducing turbulent blood flow within the stent. In some embodiments the inner layer may be comprised of electrospun PTFE with an average pore size of about 1 microns to about 12 microns, such as from about 2 microns to about 8 microns, or from about 3 microns to about 5 microns, or alternatively from about 3.5 to about 4.5 microns.

FIG. 6B illustrates a cross sectional view of a stent with an outer layer 210, an inner layer 220, and a wire scaffold 110. Additionally, the location between the outer layer 210 and the inner layer 220 is illustrated as 230. It will be appreciated that in embodiments where there are only two layers, there may not be a gap between the two layers, but the outer layer 210 and inner layer 220 may be in direct contact where they are not separated by the wire 110.

In other embodiments a third layer may be disposed in the location 230 between the outer layer 210 and the inner layer 220. In some embodiments this layer may be a "tie layer" configured to promote bonding between the outer layer 210 and the inner layer 220. In other embodiments the tie layer may further be configured to provide certain properties to the stent as a whole, such as stiffness or tensile strength. Furthermore, in embodiments where both the inner layer 220 and the outer layer 210 are porous in nature, the tie layer may be configured to create an impermeable layer between the two porous layers. In such embodiments the stent may permit cell growth and healing on both the inner and outer surfaces of the stent while still preventing tissue from outside the stent from growing into the lumen and occluding the lumen.

The tie layer may consist of any thermoplastic and may or may not be electrospun. In one embodiment, the tie layer may be expanded PTFE. In another it may be electrospun PTFE. In other embodiments it may be FEP, including electrospun FEP and FEP applied as a film or dip coating. Furthermore, the tie layer may consist of any of the following polymers or any other thermoplastic: dextran, alginates, chitosan, guar gum compounds, starch, polyvinylpyridine compounds, cellulosic compounds, cellulose ether, hydrolyzed polyacrylamides, polyacrylates, polycarboxylates, polyvinyl alcohol, polyethylene oxide, polyethylene glycol, polyethylene imine, polyvinylpyrrolidone, polyacrylic acid, poly(methacrylic acid), poly(itaconic acid), poly(2-hydroxyethyl acrylate), poly(2-(dimethylamino)ethyl methacrylate-co-acrylamide), poly(N-isopropylacrylamide), poly (2-acrylamido-2-methyl-1-propanesulfonic acid), poly (methoxyethylene), poly(vinyl alcohol), poly(vinyl alcohol) 12% acetyl, poly(2,4-dimethyl-6-triazinylethylene), poly (3morpholinylethylene), poly(N-1,2,4-triazolyethylene), poly (vinyl sulfoxide), poly(vinyl amine), poly(N-vinyl pyrrolidone-co-vinyl acetate), poly(g-glutamic acid), poly(N-propanoyliminoethylene), poly(4-amino-sulfo-aniline), poly

[N-(p-sulphophenyl)amino-3-hydroxymethyl-1,4phenyleneimino-,1,4-phenylene], isopropyl cellulose, hydroxyethyl, hydroxylpropyl cellulose, cellulose acetate, cellulose nitrate, alginic ammonium salts, i-carrageenan, N-[(3'-hydroxy-2', 3'-dicarboxy)ethyl]chitosan, konjac glocomannan, pullulan, xanthan gum, poly(allyammonium chloride), poly(allyammonium phosphate), poly(diallydimethylammonium chloride), poly(benzyltrimethylammonium chloride), poly(dimethyldodecyl(2-acrylamidoethyly) ammonium bromide), poly(4-N-butylpyridiniumethylene iodine), poly(2-N-methylpridinium methylene iodine), poly(N methylpryidinium-2,5-diylethenylene), polyethylene glycol polymers and copolymers, cellulose ethyl ether, cellulose ethyl hydroxyethyl ether, cellulose methyl hydroxyethyl ether, poly(I-glycerol methacrylate), poly(2-ethyl-2-oxazoline), poly(2-hydroxyethyl methacrylate/methacrylic acid) 90:10, poly(2-hydroxypropyl methacrylate), poly(2-methacryloxyethyltrimethylammonium bromide), poly(2-vinyl1-methylpyridinium bromide), poly(2-vinylpyridine N-oxide), poly(2-vinylpyridine), poly(3-chloro-2-hydroxypropyl 2-methacryloxyethyldimethylammonium chloride), poly(4vinylpyridine N-oxide), poly(4-vinylpyridine), poly (acrylamide/2-methacryloxyethyltrimethylammonium bromide) 80:20, poly(acrylamide/acrylic acid), poly(allylamine hydrochloride), poly(butadiene/maleic acid), poly(diallyldimethylammonium chloride), poly(ethyl acrylate/acrylic acid), poly(ethylene glycol) bis(2-aminoethyl), poly (ethylene glycol) monomethyl ether, poly(ethylene glycol)bisphenol A diglycidyl ether adduct, poly(ethylene oxide-bpropylene oxide), poly(ethylene/acrylic acid) 92:8, poly(llysine hydrobromide), poly(l-lysine hydrobromide), poly (maleic acid), poly(n-butyl acrylate/2methacryloxyethyltrimethylammonium bromide), poly(Niso-propylacrylamide), poly (N-vinylpyrrolidone/2dimethylaminoethyl methacrylate), dimethyl sulfatequaternary, poly(N-vinylpyrrolidone/vinyl acetate), poly(oxyethylene) sorbitan monolaurate (Tween 20®), poly (styrenesulfonic acid), poly(vinyl alcohol), N-methyl-4(4'formylstyryl)pyridinium, methosulfate acetal, poly(vinyl methyl ether), poly(vinylamine) hydrochloride, poly(vinylphosphonic acid), poly(vinylsulfonic acid) sodium salt and polyaniline.

Regardless of the material, the tie layer may or may not be electrospun. Further, in certain embodiments the stent may consist of two or more tie layers. The tie layer may be formed in any manner known in the art and attached to the inner and outer layers in any manner known in the art. For example, the tie layer may comprise a sheet of material which is wrapped around the inner layer 210 or a tube of material which is slipped over the inner layer 210 which is then heat shrunk or otherwise bonded to the inner and outer layers. Further, in embodiments where the tie layer is electrospun, it may be electrospun directly onto the inner layer 210, the scaffolding, or both. In some instances the tie layer may be melted after the stent is constructed to bond the tie layer to adjacent layers of the stent covering.

Furthermore, tie layers may be configured to change the overall properties of the stent covering. For example, in some instances a cover comprised solely of electrospun PTFE (of the desired pore size) may not have desired tensile or burst strength. A tie layer comprised of a relatively stronger material may be used to reinforce the PTFE inner layer, the PTFE outer layer, or both. For example, in some instances FEP layers may be used to increase the material strength of the cover.

It will also be appreciated that one or more layers of electrospun PTFE may be used in connection with a scaffolding structure other than that disclosed herein. In other words, the disclosure above relating to covers, layers, tie layers, and related components is applicable to any type of scaffolding structure as well as to stents or grafts with no separate scaffolding structure at all.

FIG. 7 illustrates a cross section of a stent 100 disposed within a body lumen 50. The stent includes wire scaffolding 110 and a cover 200. In embodiments where the cover 200 is composed of an outer layer and an inner layer, the outer layer may be disposed adjacent to the body lumen while the inner layer may be disposed toward the inside portion of the body lumen. In particular, in embodiments where the stent is not substantially tubular in shape, the outer cover layer may be defined as the layer disposed adjacent the body lumen wall and the inner cover layer defined as the layer disposed toward the inner portion of the body lumen.

In some embodiments, a cover 200 may be formed by electrospinning a membrane onto a spinning mandrel. In other words, the collection device may comprise a mandrel, such as a substantially cylindrical mandrel, which rotates during the electrospinning process. Varying the speed at which the mandrel rotates may influence certain properties of the membrane. For example, in some embodiments, the density of the membrane (and thereby the average pore size) may be related to the rotational speed of the mandrel. Further, the directionality of the fibers, or the degree to which the fibers are deposited in a more controlled direction or manner, may be related to the rotational speed of the mandrel. In some instances a collection mandrel may rotate at rates between about 1 RPM and about 500 RPM during the elctrospinning process, including rates from about 1 RPM to about 50 RPM or at about 25 RPM. A membrane of electrospun PTFE formed onto a spinning mandrel may thus comprise a tubular membrane having no seam and substantially isotropic properties.

Once a membrane has been electrospun onto a mandrel, the membrane may then be sintered. In the case of PTFE, the membrane may be sintered at temperatures of about 385 degrees C., including temperatures from about 360 degrees C. to about 400 degrees C. Sintering may tend to set the structure of the PTFE, meaning sintering reduces the softness or flowability of the PTFE. Furthermore, sintering may evaporate any water or PEO mixed with the PTFE, resulting in a material comprised substantially of pure PTFE.

In some embodiments, a PTFE layer may be spun onto a mandrel and then sintered. Once the membrane is sintered, the tube of material may be removed from the mandrel, then slid back on the mandrel (to initially break any adherence of the membrane to the mandrel). In other instances, low friction coatings may alternatively or additionally be applied to the mandrel before the membrane is electrospun. Once the membrane is reapplied to the mandrel, a wire scaffolding can be formed over the mandrel and the membrane. A second layer of material may then be spun onto the scaffolding and the membrane, and subsequently sintered. Additionally layers may also be added.

In some instances, the layers may comprise a first layer of PTFE, a second layer of FEP, and a third layer of PTFE. The properties of each of these layers, including average pore size, may be controlled to form coating that inhibit growth of tissue through a particular layer or that permits endothelial growth on a particular layer.

In another example, a first layer of PTFE may be spun on a mandrel, sintered, removed from the mandrel, replaced and the mandrel, and a scaffolding structure applied. An FEP layer may then be applied by dipping, spraying, application of a film layer, electrospinning, or other processing. The FEP layer may or may not be sintered before applying an outer PTFE layer.

In another particular example, a first layer of PTFE may again be spun on a mandrel, sintered, removed, replaced, and a scaffolding structure applied. An FEP layer may then be applied as a film layer. In some instances it may be "tacked" into place, for example by a soldering iron. An outer tube of PTFE (which may be formed separately by electrospinning onto a mandrel and sintering) may then be disposed over the FEP film layer. The entire construct may then be pressured, for example by applying a compression wrap. In some embodiments this wrap may comprise any suitable material, including a PTFE based material. In other embodiments a Kapton film may be wrapped around the construct before the compression wrap, to prevent the construct from adhering to the compression wrap.

The compressed layers may then be heated above the melting temperature of the FEP, but below the sintering temperature of the PTFE. For example, the melt temperature of the FEP may be from about 300 degrees C. to about 330 degrees C., including about 325 degrees C. PTFE may be sintered at temperatures from about 360 degrees C. to about 400 degrees C. Thus, the entire construct may be heated to an appropriate temperature such as about 325 degrees C. In some embodiments the construct may be held at this temperature for about 15 to about 20 minutes. This may allow the FEP to "flow" into the porous PTFE nanofiber layers surrounding the FEP. The joining of the FEP tie layer to the PTFE outer and inner cover layers may increase the strength of the finished covering. The construct may then be cooled and the compression wrap and the Kaptron film discarded. The construct may then be removed from the mandrel.

A stent formed by the exemplary process described above may be configured with desired characteristics of porosity and strength. In some instances the FEP material may coat the PTFE nanofibers, but still allow for porosity which permits endothelial growth. The degree to which the FEP coats the PTFE may be controlled by the temperature and time of processing. The lower the temperature and/or the shorter the time the construct is held at temperature, the less the FEP may flow. In some instances a tie layer of FEP which is impervious the tissue growth through the layer may be formed by heating the construction only to about 260 degrees C.

Additionally, in some embodiments a stent may also include a cuff at one or both ends of the stent. The cuff may be an additional coating on the outside diameter of the stent, disposed adjacent one of the ends of the stent. The cuff may be configured to promote rapid cellular ingrowth into the cuff; for example the cuff may be more porous than the outer layer of the covering of the stent. Factors such as porosity, type of coating, type of material, use of organic material, and/or use or composite materials formed of synthetic material and organic material may be used to create a cuff configured for rapid tissue ingrowth. Again, the cuff may be configured to promote rapid growth or endothelization at one or both ends of the stent. In some embodiments cuffs may be disposed adjacent both ends of the stent. The cuff or cuffs may tend to "anchor" the ends of the stent with respect to the vessel walls, reducing the relative movement of the stent ends with respect to the vessel walls. Such a reduction in movement may lessen irritation of the vessel by the stent ends, minimizing complications such as stenosis. Cuffs may be configured for use in CVO type applications in some instances.

In some embodiments, the outer layer of the covering of the stent may be relatively non-porous to limit tissue growth through the layer, but the cuff, disposed about the outer cover layer may provide a section near each end at which some ingrowth may occur.

The cuff may be comprised of an electrospun material, such as PTFE, and may be bonded to the outer covering layer through any method, including methods described herein. For example, a layer of FEP may be disposed between the outer covering layer and the cuff and heated to bond the layers. In other embodiments the cuff may comprise a collagen layer which is glued to the stent. Further, a co-electrospun collagen and PTFE cuff may be utilized.

FIGS. 8A-9D are scanning electron micrograph (SEM) images of an exemplary embodiment of a stent covering. FIGS. 8A-8D are images of the outer layer of the covering while FIGS. 9A-9D are images of the inner layer of the covering. For each SEM, the electrospun PTFE was covered with a very thin layer of gold in order to make the structure visible on an SEM image.

Figure 8A:
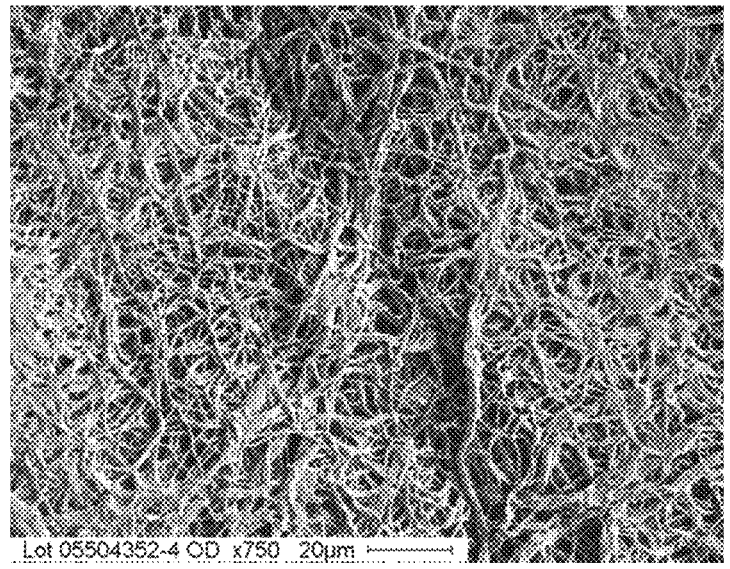
FIGS. 8A-8D are scanning electron micrograph ("SEM") images of one embodiment of an electrospun PTFE outer covering for a stent.
Figure 8B:
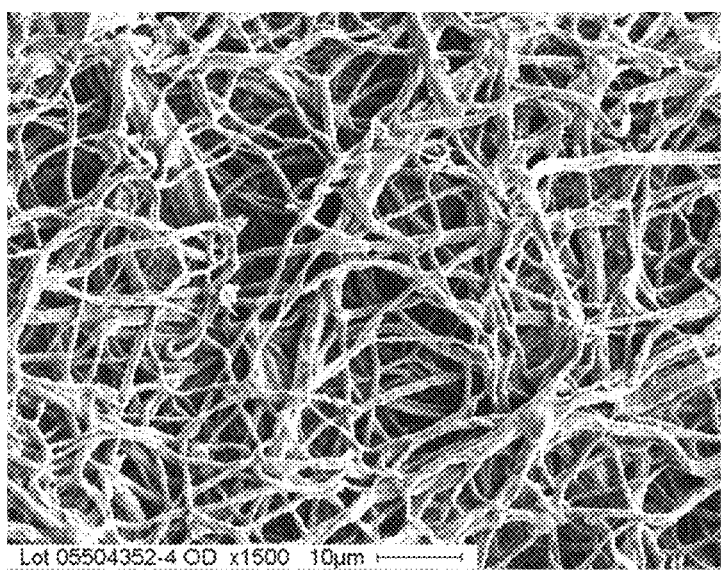
Figure 8C:
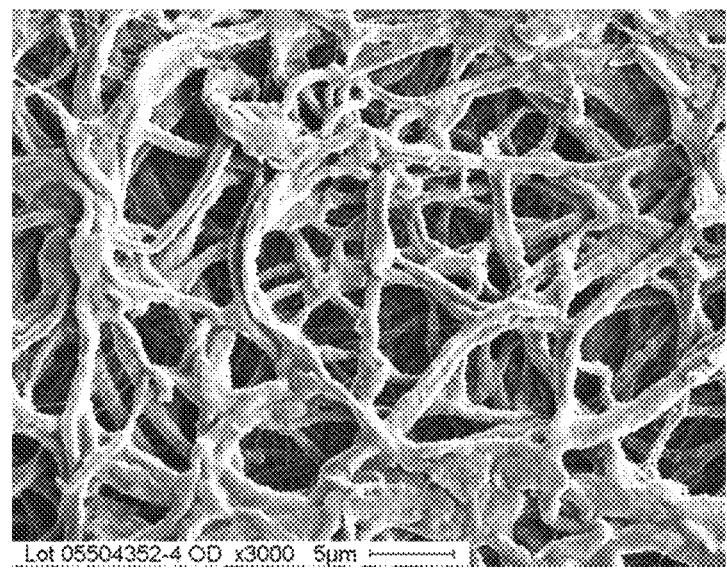
Figure 8D:
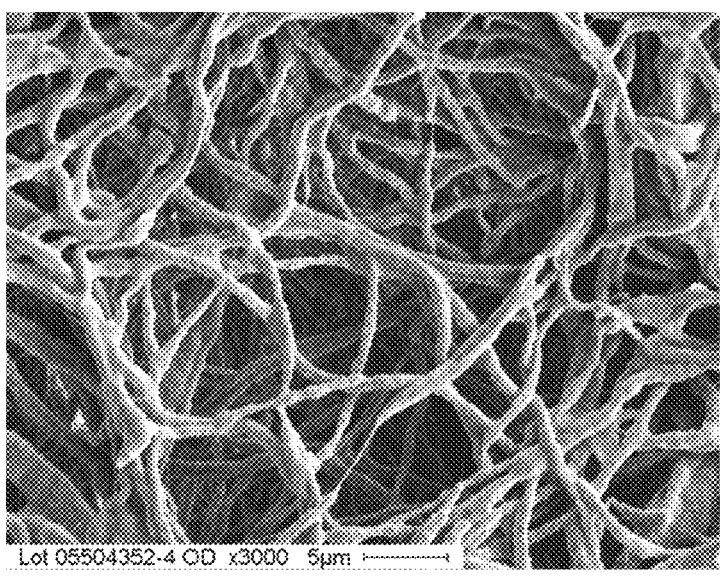
Figure 9A:
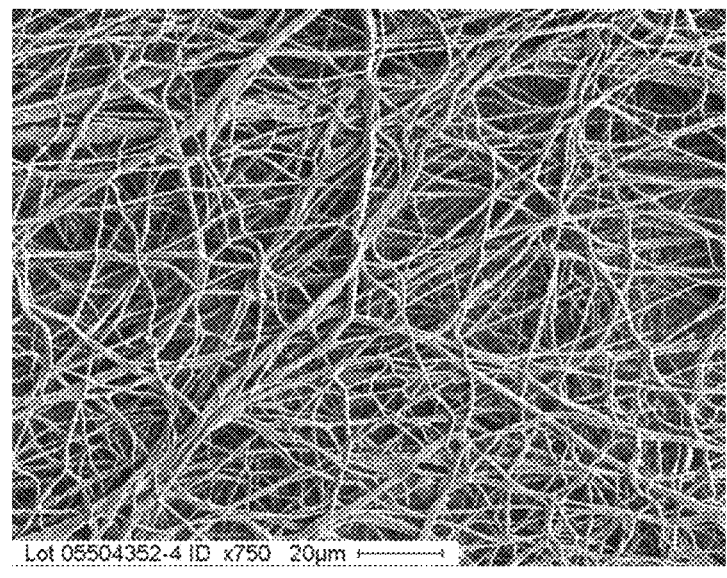
FIGS. 9A-9D are SEM images of an electrospun PTFE inner layer of the covering of the stent of FIG. 8A-8D.
Figure 9B:
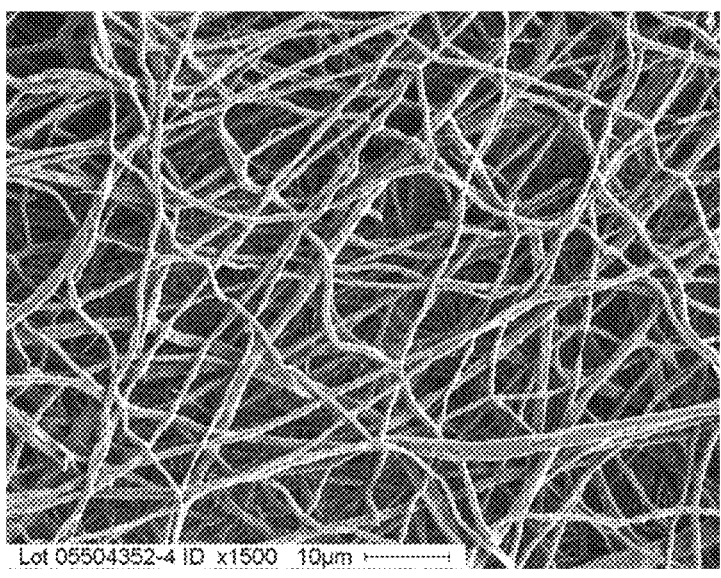
Figure 9C:
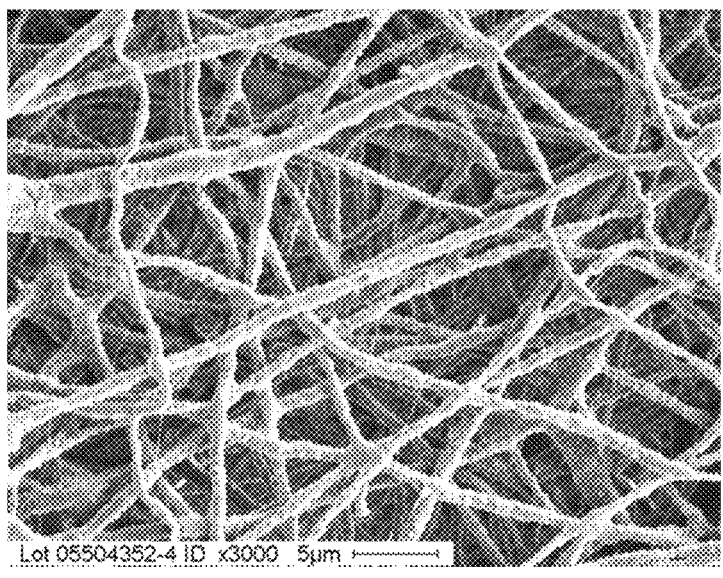
Figure 9D:
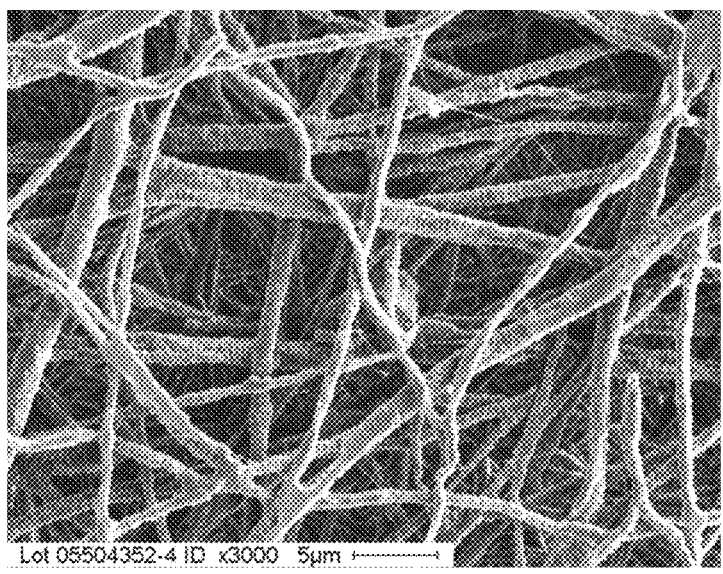

FIG. 8A is an SEM image of the outer covering at 750× magnification, FIG. 8B an SEM image at 1500× magnification, and FIGS. 8C and 8D at 3000× magnification. Similarly, FIG. 9A is an image of the inner covering at 750× magnification, FIG. 9B at 1500× magnification, and FIGS. 9C and 9D at 3000× magnification.

These SEM images reflect the microstructure of electrospun PTFE, depicting the randomly deposited criss-crossing branches of PTFE that form the covering.

FIGS. 10A-11D are scanning electron micrograph (SEM) images of a second exemplary embodiment of a stent covering. FIGS. 10A-10D are images of the outer layer of the covering while FIGS. 11A-11D are images of the inner layer of the covering. Again, for each SEM, the electrospun PTFE was covered with a very thin layer of gold in order to make the structure visible on an SEM image.

Figure 10A:
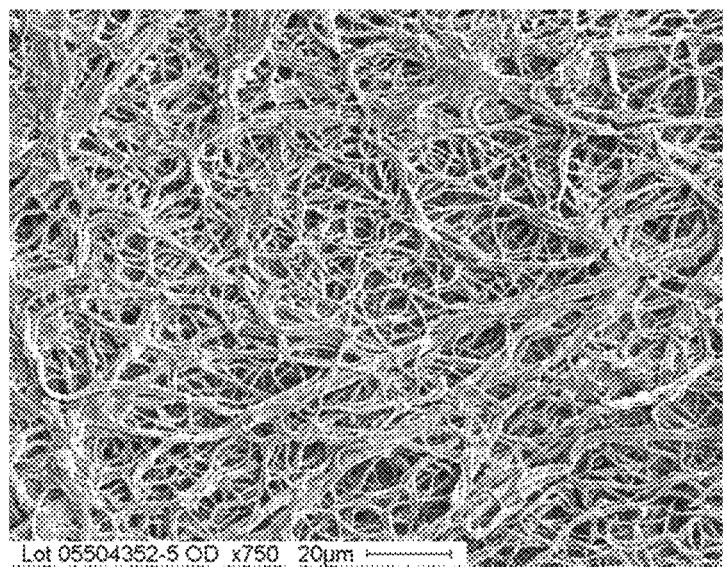
FIGS. 10A-10D are SEM images of an electrospun PTFE outer covering of another embodiment of a stent.
Figure 10B:
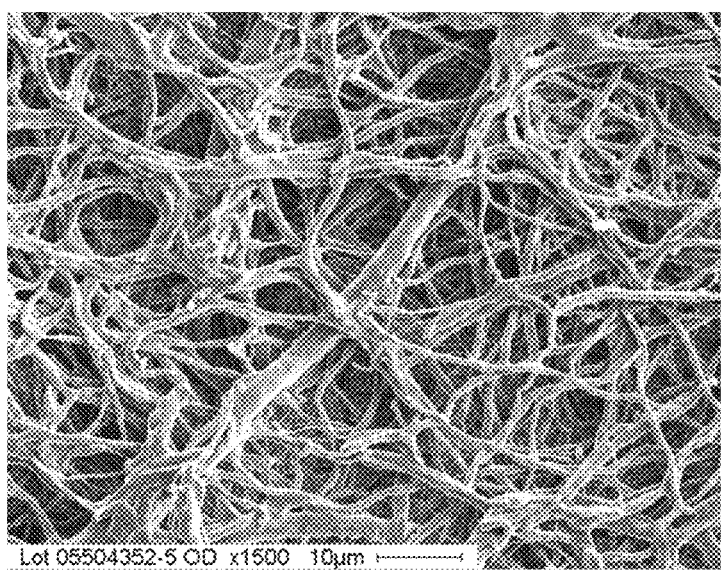
Figure 10C:
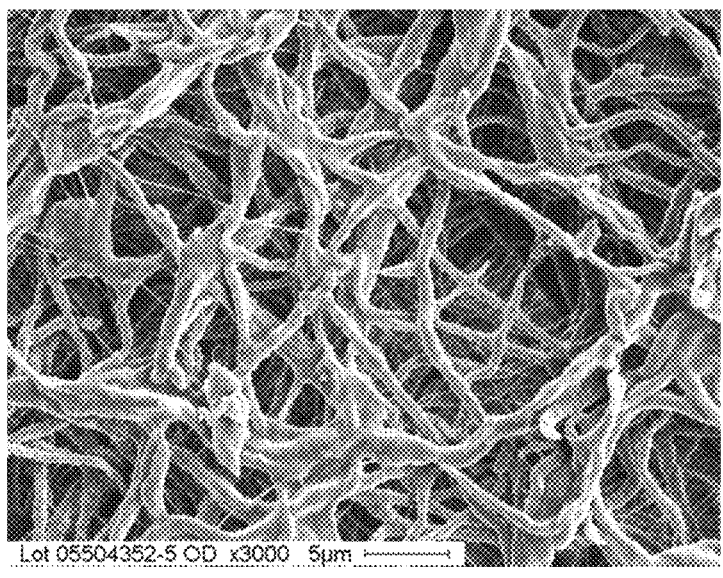
Figure 10D:
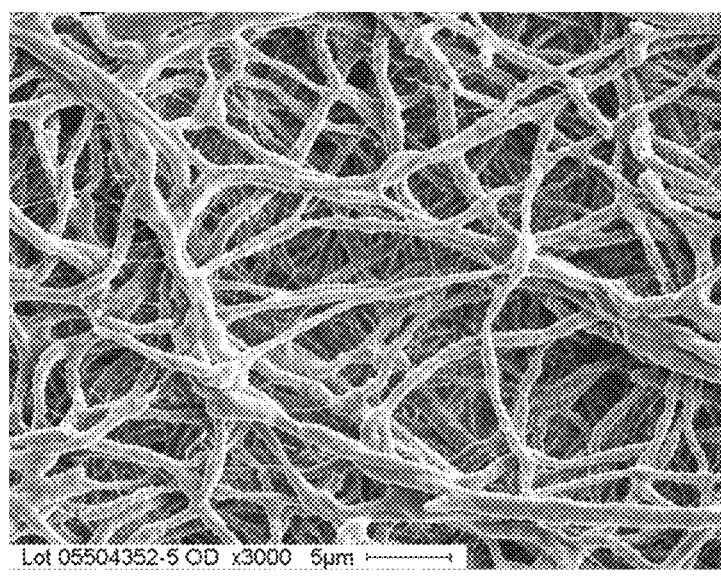
Figure 11A:
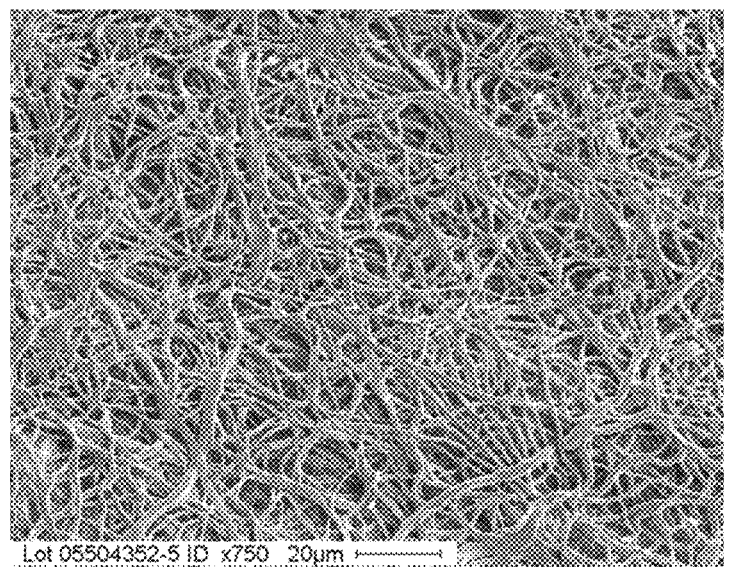
FIGS. 11A-11D are SEM images of an electrospun PTFE inner layer of the covering of the stent of FIG. 10A-10D.
Figure 11B:
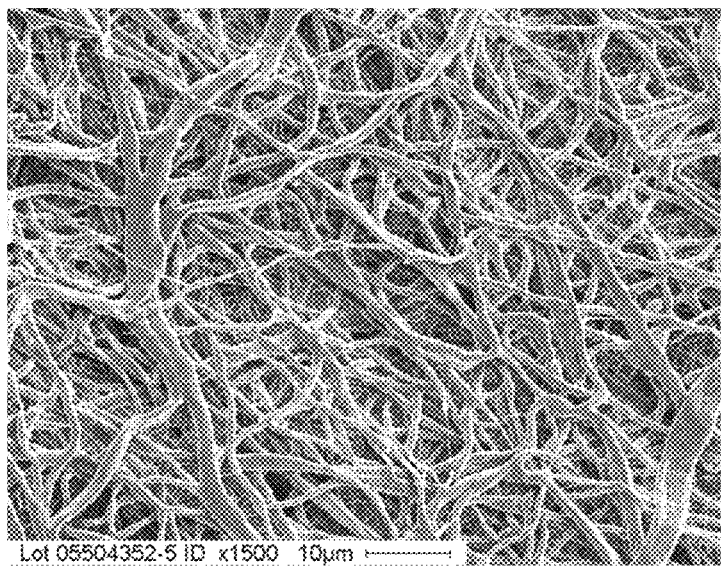
Figure 11C:
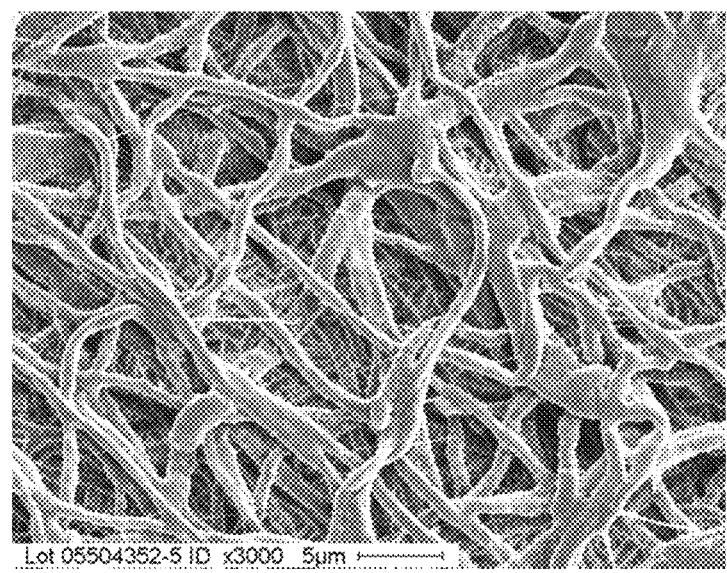
Figure 11D:
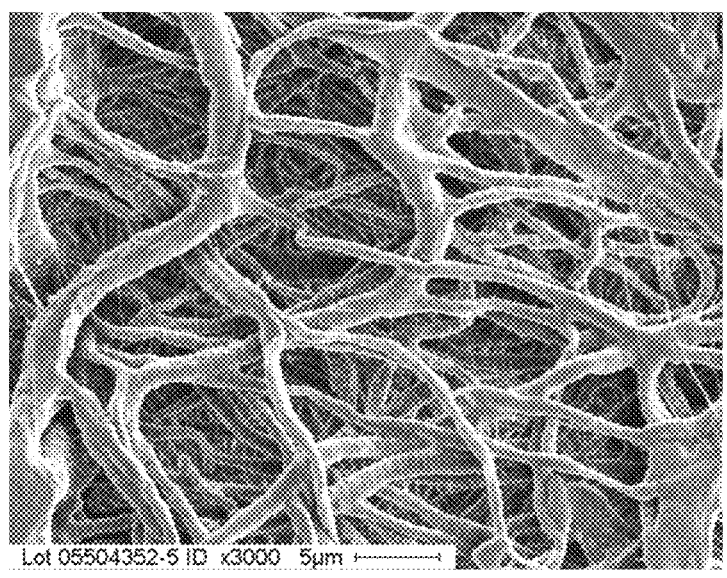

FIG. 10A is an SEM image of the outer covering at 750× magnification, FIG. 10B an SEM image at 1500× magnification, and FIGS. 10C and 10D at 3000× magnification. Similarly, FIG. 11A is an image of the inner covering at 750× magnification, FIG. 11B at 1500× magnification, and FIGS. 11C and 11D at 3000× magnification.

While specific embodiments of stents have been illustrated and described, it is to be understood that the disclosure provided is not limited to the precise configuration and components disclosed. Various modifications, changes, and variations apparent to those of skill in the art having the benefit of this disclosure may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill, having the benefit of this disclosure, in the art that changes may be made to the details of the above-described embodiments without departing from the underlying principles of the disclosure herein.

The invention claimed is:

1. A covered stent, comprising:
a scaffolding structure comprising a midsection and a first end section and a second end section,
wherein a compressibility of the first end section is greater than a compressibility of the midsection, wherein the midsection comprises a first plurality of apexes and the first end section comprises a second plurality of apexes,
wherein the second end section comprises a third plurality of apexes,
wherein each of the first plurality of apexes is nested within an adjacent apex of the first plurality of apexes, and
wherein each of the second plurality of apexes and the third plurality of apexes is non- nested relative to an adjacent apex of the second plurality of apexes and the third plurality of apexes; and
a cover coupled to the scaffolding structure, comprising:
an inner layer of electrospun polytetrafluoroethylene (PTFE);
an outer layer of electrospun PTFE; and
a tie layer disposed between the inner layer and the outer layer,
wherein the scaffolding structure is disposed between the inner layer and the outer layer.

2. The covered stent of claim 1,
wherein a first apex distance between each apex of the first plurality of apexes is less than a second apex distance between each apex of the second plurality of apexes.

3. The covered stent of claim 2,
wherein a third apex distance between each of the third plurality of apexes is greater than the first apex distance.

4. The covered stent of claim 3, wherein one or more of the first apex distance, the second apex distance, and the third apex distance incrementally increases from a longitudinal midpoint of the scaffolding structure toward ends of the scaffolding structure.

5. The covered stent of claim 1, wherein the midsection comprises a first plurality of arms and the first end section comprises a second plurality of arms; and
wherein a first arm length of each of the first plurality of arms is less than a second arm length of each of the second plurality of arms.

6. The covered stent of claim 5,
wherein the second end section comprises a third plurality of arms, and
wherein a third arm length of each of the third plurality of arms is greater than the first arm length.

7. The covered stent of claim 6, wherein one or more of the first arm length, the second arm length, and the third arm length incrementally increases from a longitudinal midpoint of the scaffolding structure toward ends of the scaffolding structure.

8. The covered stent of claim 2, wherein a first inside arc diameter of each of the first plurality of apexes is less than a second inside arc diameter or each of the second plurality of apexes.

9. The covered stent of claim 8,
wherein a third arc diameter of each of the third plurality of apexes is greater than the first arc diameter.

10. The covered stent of claim 9, wherein one or more of the first arc diameter and the second arc diameter incrementally increases from a longitudinal midpoint of the scaffolding structure toward ends of the scaffolding structure.

11. A covered stent, comprising:
a scaffolding structure comprising a midsection and a first end section,
wherein a compressibility of the first end section is greater than a compressibility of the midsection;

| wherein the midsection comprises a first plurality of apexes and a first plurality of arms;

wherein the first end section comprises a second plurality of apexes and a second plurality of arms;

wherein a first apex distance between each apex of the first plurality of apexes is less than a second apex distance between each apex of the second plurality of apexes;

wherein a first inside arc diameter of each of the first plurality of apexes is less than a second inside arc diameter or each of the second plurality of apexes; and wherein a first arm length of each of the first plurality of arms is less than a second arm length of each of the second plurality of arms; and a cover coupled to the scaffolding structure, comprising:

an inner layer of electrospun PTFE;

an outer layer of electrospun PTFE; and a tie layer disposed between the inner layer and the outer layer, wherein the scaffolding structure is disposed between the inner layer and the outer layer.

12. A covered stent, comprising:

a scaffolding structure comprising a midsection and a first end section and a second end section, wherein a compressibility of the first end section is greater than a compressibility of the midsection, wherein the midsection comprises a first plurality of apexes and the first end section comprises a second plurality of apexes, wherein a first inside arc diameter of each of the first plurality of apexes is less than a second inside arc diameter or each of the second plurality of apexes; and a cover coupled to the scaffolding structure, comprising:

an inner layer of electrospun polytetrafluoroethylene (PTFE);

an outer layer of electrospun PTFE; and a tie layer disposed between the inner layer and the outer layer, wherein the scaffolding structure is disposed between the inner layer and the outer layer.

* * * * *